(12) United States Patent
Lesterhuis et al.

(10) Patent No.: US 11,186,640 B2
(45) Date of Patent: Nov. 30, 2021

(54) METHOD FOR THE IDENTIFICATION OF IMMUNOTHERAPY-DRUG COMBINATIONS USING A NETWORK APPROACH

(71) Applicant: THE UNIVERSITY OF WESTERN AUSTRALIA, Nedlands (AU)

(72) Inventors: Willem Joost Lesterhuis, Nedlands (AU); Richard Andrew Lake, Nedlands (AU); Anthony Bosco, Subiaco (AU)

(73) Assignee: THE UNIVERSITY OF WESTERN AUSTRALIA, Crawley (AU)

( * ) Notice: Subject to any disclaimer, the term of this patent is extended or adjusted under 35 U.S.C. 154(b) by 965 days.

(21) Appl. No.: 15/500,498

(22) PCT Filed: Jul. 31, 2015

(86) PCT No.: PCT/AU2015/000458
§ 371 (c)(1),
(2) Date: Jan. 30, 2017

(87) PCT Pub. No.: WO2016/015095
PCT Pub. Date: Feb. 4, 2016

(65) Prior Publication Data
US 2017/0218068 A1 Aug. 3, 2017

(30) Foreign Application Priority Data
Jul. 31, 2014 (AU) ................. 2014902956

(51) Int. Cl.
| | | |
|---|---|---|
| *A61K 39/395* | (2006.01) |
| *A61K 31/203* | (2006.01) |
| *A61K 31/55* | (2006.01) |
| *A61P 35/00* | (2006.01) |
| *A61K 31/21* | (2006.01) |
| *C07K 16/28* | (2006.01) |
| *G16B 5/00* | (2019.01) |
| *G16B 20/00* | (2019.01) |
| *A61K 31/34* | (2006.01) |
| *A61K 45/06* | (2006.01) |
| *A61K 31/445* | (2006.01) |
| *A61K 31/495* | (2006.01) |
| *G16B 20/20* | (2019.01) |
| *A61K 31/198* | (2006.01) |
| *A61K 31/216* | (2006.01) |
| *A61K 31/382* | (2006.01) |
| *A61K 31/409* | (2006.01) |
| *A61K 31/4415* | (2006.01) |
| *A61K 31/4468* | (2006.01) |
| *A61K 31/453* | (2006.01) |
| *A61K 31/506* | (2006.01) |
| *A61K 31/551* | (2006.01) |
| *A61K 31/58* | (2006.01) |
| *A61K 38/17* | (2006.01) |
| *A61K 39/00* | (2006.01) |

(52) U.S. Cl.
CPC ........ *C07K 16/2818* (2013.01); *A61K 31/198* (2013.01); *A61K 31/203* (2013.01); *A61K 31/21* (2013.01); *A61K 31/216* (2013.01); *A61K 31/34* (2013.01); *A61K 31/382* (2013.01); *A61K 31/409* (2013.01); *A61K 31/445* (2013.01); *A61K 31/4415* (2013.01); *A61K 31/4468* (2013.01); *A61K 31/453* (2013.01); *A61K 31/495* (2013.01); *A61K 31/506* (2013.01); *A61K 31/55* (2013.01); *A61K 31/551* (2013.01); *A61K 31/58* (2013.01); *A61K 38/1793* (2013.01); *A61K 39/3955* (2013.01); *A61K 45/06* (2013.01); *C07K 16/2878* (2013.01); *G16B 5/00* (2019.02); *G16B 20/00* (2019.02); *G16B 20/20* (2019.02); *A61K 2039/505* (2013.01); *A61K 2039/55* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 5,700,830 A * | 12/1997 | Korthuis | ................ | A61K 31/14 514/426 |
| 6,610,660 B1 * | 8/2003 | Saavedra | ............. | C07D 239/34 514/25 |
| 6,689,810 B2 * | 2/2004 | Martin | .................... | A61P 11/00 514/492 |
| 6,946,484 B2 * | 9/2005 | Adams | ................. | A61K 31/198 514/509 |

(Continued)

FOREIGN PATENT DOCUMENTS

WO    2012/095505 A1    7/2012

OTHER PUBLICATIONS

Burke et al. 2013 Carcinogenesis 34: 503-512.*

(Continued)

*Primary Examiner* — Ilia I Ouspenski
(74) *Attorney, Agent, or Firm* — Much Shelist, PC; Christopher M. Cabral

(57) ABSTRACT

This invention relates to systems and methods for evaluating the differentiality of a set of discrete random variables between two or more conditions, such as a malignant condition responding to treatment regime and one that is not. It also provides for the identification and selection of drugs that act in coordinated manner to phenocopy a genetic network of a malignant condition that responds to at least an immune checkpoint blockade agent.

24 Claims, 17 Drawing Sheets

(56) References Cited

U.S. PATENT DOCUMENTS

| | | | | |
|---|---|---|---|---|
| 7,678,391 | B2* | 3/2010 | Graham | A61K 31/198 424/718 |
| 8,404,665 | B2* | 3/2013 | Shami | A61K 31/704 514/150 |
| 8,410,175 | B2* | 4/2013 | Yasuda | A61K 31/34 514/645 |
| 8,673,914 | B2* | 3/2014 | Chen | A61K 31/277 514/243 |
| 8,728,474 | B2* | 5/2014 | Honjo | C07K 14/70521 424/144.1 |
| 8,784,795 | B2* | 7/2014 | Watson | A61K 45/06 424/85.1 |
| 2002/0001615 | A1* | 1/2002 | Nanus | A61K 38/21 424/450 |
| 2002/0076434 | A1* | 6/2002 | Williams | A61K 9/127 424/450 |
| 2003/0124127 | A1* | 7/2003 | Yang | C07K 16/2893 424/146.1 |
| 2005/0131063 | A1* | 6/2005 | Stamler | A61K 2300/00 514/509 |
| 2007/0237779 | A1* | 10/2007 | Ledbetter | C07K 16/2809 424/155.1 |
| 2008/0025972 | A1* | 1/2008 | Daaka | A61K 31/16 424/130.1 |
| 2009/0131425 | A1* | 5/2009 | Michaelides | A61P 35/00 514/233.2 |
| 2009/0142337 | A1* | 6/2009 | Squires | A61K 38/09 424/130.1 |
| 2009/0143399 | A1* | 6/2009 | Hurley | C07D 403/14 514/252.16 |
| 2010/0221247 | A1* | 9/2010 | Bender | A61K 39/3955 424/133.1 |
| 2010/0227838 | A1* | 9/2010 | Shah | C12Q 1/6886 514/89 |
| 2011/0182978 | A1* | 7/2011 | Shami | A61K 31/655 424/450 |
| 2011/0257893 | A1 | 10/2011 | Taylor et al. | |
| 2012/0121604 | A1* | 5/2012 | Jure-Kunkel | A61K 31/555 424/142.1 |
| 2013/0004481 | A1* | 1/2013 | Solca | A61P 13/08 424/133.1 |
| 2013/0243731 | A1* | 9/2013 | Dias | A61K 45/06 424/93.2 |
| 2014/0099254 | A1 | 4/2014 | Chang et al. | |
| 2014/0286973 | A1* | 9/2014 | Powell, Jr. | A61K 39/0011 424/185.1 |
| 2014/0294765 | A1* | 10/2014 | Cojocaru | A61P 29/00 424/85.2 |
| 2014/0294806 | A1* | 10/2014 | Karmali | A61K 31/513 424/133.1 |
| 2014/0341917 | A1* | 11/2014 | Nastri | A61K 39/0011 424/139.1 |
| 2014/0363442 | A1* | 12/2014 | Frazier | A61P 19/00 424/143.1 |
| 2015/0118222 | A1* | 4/2015 | Levy | A61P 35/00 424/130.1 |
| 2015/0139937 | A1* | 5/2015 | Gendelman | A61K 38/193 424/85.1 |
| 2015/0166661 | A1* | 6/2015 | Chen | A61K 31/573 424/135.1 |
| 2015/0190506 | A1* | 7/2015 | Cheung | C07K 16/2878 424/134.1 |
| 2015/0210769 | A1* | 7/2015 | Freeman | G01N 33/57484 424/136.1 |
| 2015/0290092 | A1* | 10/2015 | Shieh | A61K 9/5161 424/401 |
| 2015/0290224 | A1* | 10/2015 | Shami | A61K 9/1075 514/150 |
| 2015/0297695 | A1* | 10/2015 | Bae | A61P 13/08 424/85.1 |
| 2015/0377882 | A1* | 12/2015 | Ashdown | G01N 33/543 424/184.1 |
| 2017/0000787 | A1* | 1/2017 | Sebti | C07D 295/135 |
| 2017/0112800 | A1* | 4/2017 | Roy | A61K 47/554 |
| 2017/0190675 | A1* | 7/2017 | Chen | A61K 31/166 |
| 2021/0015857 | A1* | 1/2021 | Lesterhuis | C07K 16/2878 |

OTHER PUBLICATIONS

Su et al. 2010 Int. J. Radiation Oncology Biol. Phys. 77: 559-565.*
Zappasodi et al. 2019 Nature Medicine 25: 759-766.*
SR11237—Sigma-Aldrich Catalog (2021), 4 pages.*
Hamid, O., et al., "A Prospective Phase II Trial Exploring the Association Between Tumor Microenvironment Biomarkers and Clinical Activity of Ipilimumab in Advanced Melanoma," Journal of Translational Medicine, vol. 9, No. 204, pp. 1-16 (Nov. 28, 2011).
Lesterhuis, W. J., et al., "Synergistic Effect of CTLA-4 Blockade and Cancer Chemotherapy in the Induction of Anti-Tumor Immunity," PLOS One, vol. 8, Issue 4, e61895, pp. 1-8 (Apr. 2013).
Vitali, Francesca, et al., "Network-based Target Ranking for Polypharmacological Therapies," Journal of Biomedical Informatics, vol. 46, pp. 876-881 (Oct. 2013).
Extended European Search Report for EP 15827186.6 dated Jun. 22, 2018.
Lesterhuis, W. Joost., et al., "Network Analysis of Immunotherapy-Induced Regressing Tumours Identifies Novel Synergistic Drug Combinations," Nature, Scientific Reports, 5, Article No. 12298 (Jul. 21, 2015).

* cited by examiner upregulated in responders downregulated in responders

METHOD FOR THE IDENTIFICATION OF IMMUNOTHERAPY-DRUG COMBINATIONS USING A NETWORK APPROACH

CROSS REFERENCE TO RELATED APPLICATIONS

The present application is the 35 U.S.C. 371 National Stage of International Application No. PCT/AU2015/000458, filed Jul. 31, 2015, which claims priority from Australian patent application 2014902956, filed Jul. 31, 2014, the contents of which are incorporated by reference.

TECHNICAL FIELD

This invention relates to systems and methods for evaluating the differentiality of a set of discrete random variables between two or more conditions, such as a malignant condition responding to treatment regime and one that is not. In particular embodiments, the systems and methods more specifically relate to identifying and evaluating the relationships between a plurality of genes that are activated or repressed in a malignant condition responding to treatment regime. In further embodiments the invention provides for the identification and selection of therapeutic agents that phenocopy the genetic network of a malignant condition that responds to at least an immune checkpoint blockade agent. Specifically, these therapeutic agents work in concert with immune checkpoint blockade to modulate a module or sub-module of genes that govern the response to immune checkpoint blockade. In yet a further embodiment the invention provides for the identification and selection of at least a therapeutic agent that works in concert with an immune checkpoint blockade agent to modulate at least a hub gene in a response-associated module.

BACKGROUND ART

Over the last decades many studies have pinpointed oncogenic events and cellular pathways that initiate or promote cancer formation and progression. Although compounds targeting these pathways have shown initial promise and effective drugs have been developed, their clinical benefit is often modest.

The main drawback of using a single compound targeting one pathway is the growing understanding that cellular function and behaviors are dependent on sets of pathways that interact in the context of functional modules. For this reason, a more comprehensive approach is testing differentiality for a set of pathways between conditions. Hence, the scientific community is now investigating possibilities to inhibit several pathways at the same time.

Surprisingly little is known about the events that occur during therapy-induced tumor regression. As an example, in the last few years cancer immunotherapy has been quite successful, with several novel treatments entering the clinic. The most important examples are ipilimumab, which targets the inhibitory T cell molecule CTLA-4, and nivolumab, which targets Programmed Death receptor (PD-1).

Ipilimumab is the very first drug that has ever been shown to confer an overall survival benefit in metastatic melanoma and lung cancer phase III clinical studies are ongoing with both ipilimumab and nivolumab. Importantly, subsets of patients remain disease-free for many years, and thus can be designated cured by the treatment (17% 7-year survival for melanoma after ipilimumab). However, this is only a small minority of patients; the majority of patients experience disease progression. Although some studies investigated the role of isolated cell types or specific molecules in the effector immune response after anti-CTLA-4, a comprehensive analysis of the crucial effector cells and molecules that effectively cure the tumour is lacking. Thus, it remains largely unknown why there is this dichotomy in response to anti-CTLA-4 immunotherapy. Nor is it known how exactly the immunotherapy-induced anti-tumor effector response is mediated and how it can be further amplified in order to increase efficacy.

Even more surprising is the fact that it is not exactly clear which molecular and cellular events occur during tumor regression upon classic cytotoxic chemotherapy treatment. For example, 30% of patients with esophageal cancer demonstrate a complete remission of cancer after treatment with chemoradiotherapy, while 20% have no apparent treatment effect at all, even though the clinical and pathological characteristics of the patients and cancers appear identical. Furthermore, from many studies the picture emerges that the process of chemotherapy-induced tumor regression is highly complex, and is not represented well in cellular studies in vitro. Thus, it remains enigmatic what discriminates a treatment-responsive tumor from a non-responsive tumor.

The current practice of drug discovery in cancer is based upon the assumption that the same molecular and cellular processes that build a cancer, when tackled, will kill the cancer. This has indeed been shown for several selected, single oncogene-dependent cancers. This approach invariably relies on the analysis of gene expression studies that have typically focused on identification of differentially expressed genes or pathways. However, this approach is limited, because genes do not function in isolation, they work in concert.

Over time it has become clear that in the majority of cancers therapeutic inhibition of tumour-promoting molecular pathways only temporarily leads to regression and is often followed by rapid cancer progression. This is due to the fact that molecular pathways that are different from the ones that are inhibited by the therapy can take over their tumorigenic function, and thus allow cancer cells to escape from being killed.

A new approach to the way in which genotypic and phenotypic cancer data is examined is therefore required. A significance advance in this context was the application of network graph theory to the analysis of genomic data. Yet this information alone is not sufficient to target key events that might serve as a treatment in cancer development.

It is against this background that the present invention has been developed.

The present inventors have sought to address the deficiencies in the field by focusing on the molecular and cellular events associated with resolving rather than evolving cancer. Through this approach they have been able to reinforce or mimic those events that increase the response rates to current treatments. In the past, this has not been possible because full regressions were not seen in many cancer patients. Recently, immunotherapy with immune checkpoint-blocking antibodies has shown remarkable success with full cure in a small percentage of patients.

SUMMARY OF INVENTION

The inventors have deployed gene network analysis to identify molecular interaction networks in animals responding and non-responding to cancer immunotherapy to prioritize the central genes that potentially play an important role in treatment efficacy and that are critical to the equilibrium of the resolution of a malignant condition.

The underlying concept is that a functioning biological system can be represented as a network of interconnected genes. Rather than focusing on expression levels of individual genes, network science interrogates co-expression relationships between genes; by searching for gene pairs that are expressed in a correlated fashion (positive or negative) over many samples in a dataset and connectivity between genes is then inferred. Many complex interconnected systems have a "scale-free" network architecture, meaning that the vast majority of nodes are connected to a few other nodes, whereas a few nodes are connected to many nodes, behaving as hubs that dominate the connectivity patterns and essentially "hold" the network together. Notably, hubs are crucial for the function and the persistence of cellular networks. By constructing topological maps of connections between genes and by inference, gene products, subnetworks (modules) of separate but highly connected pathways with common functions can be distinguished. Thus, network analysis allows the identification of modules and hubs that are critical to the equilibrium of complex cancer systems.

Using this approach to interrogate co-expression relationships between genes expressed in animals exhibiting responding and non-responding cancers, the inventors have developed a detailed map of the molecular networks that are associated with immuno-therapeutic success in certain cancer systems. Using this systems biology approach, they are able to identify genetic modules that govern the response to immune checkpoint blockade. Using these data they interogate publicly available databases of drug-treated cell lines to identify drugs that reinforce response-associated modules. In particular, the method of the invention provides systems to identify drugs that work in a coordinated manner with an immunotherapeutic agent (such as an immune checkpoint blockade agent) to (a) phenocopy a genetic network associated with a responding malignant condition or (b) influence a genetic hub that is pivotal to the genetic activity and or equilibrium of a malignant condition.

In some embodiments, the invention provides a computer-implemented method for identifying or evaluating relationships between gene molecular interaction networks to identify genetic modules and more specifically genetic hubs that govern the response to immune checkpoint blockade.

Further the invention provides a computer-implemented method to identify drugs that work in a coordinated manner with an immunotherapeutic agent (such as an immune checkpoint blockade agent to (a) phenocopy a genetic network associated with a responding malignant condition or (b) influence the biological activity of a genetic hub that is pivotal to the genetic activity and or equilibrium of a malignant condition.

In one aspect, the method comprises the steps of:
  a. receiving a target set of genetic materials from a plurality of animals, each either responding or non-responding to immunotherapy of a cancer condition;
  b. evaluating and searching for gene pairs that are expressed in a correlated fashion (positive or negative) over many samples in a dataset;
  c. identifying dependency network structures for the plurality of genes for each condition; and
  d. defining genetic modules and or hubs that serve as an intervention point in treatment efficacy.

The method further provides a system or process to identify drugs that work in a coordinated manner with an immunotherapy (e.g. an immune checkpoint blockade agent) to phenocopy a network of responding tumours, said method comprising the steps of
  a. interrogating publicly available databases of drug-treated cell lines with module data derived from the above method; and
  b. selecting those drugs that influence a response (positive or negative) associated with at least a module that governs and or dominates a response to immune checkpoint blockade from animals that respond to a treatment.

The method further provides a system or process to identify drugs that work in a coordinated manner with an immunotherapy (e.g. an immune checkpoint blockade agent) to phenocopy a network of responding tumours, said method comprising the step of
  a. interrogating publicly available drug databases and the biomedical literature to identify drugs that are capable of influencing the biological activity of at least a hub that is pivotal to the genetic activity and or equilibrium of a malignant condition.

The present invention further relates to therapeutic combinations that influence immune checkpoint blockade and which enhance a response to a malignant condition.

Preferably, the immune checkpoint blockade agent targets the inhibitory T cell molecule CTLA-4 and or targets the Programmed Death receptor (PD-1) or and or PD-Ligand (PD-L) pathway and or glucocorticoid-induced tumor necrosis factor receptor (GITR). An example of an agent that targets the inhibitory T cell molecule CTLA-4 is a CTLA-4 antagonist such as ipilimumab or tremelimumab. An example of an agent that targets PD-1 is a PD-1 antagonist such as nivolumab, AMP-224, pidilizumab or pembrolizumab. An example of an agent that targets PD-L1 is a PD-L1 antagonist such as MPDL-3280A, MSB0010718C or MEDI4736. Examples of agents that target GITR are antagonists such as TRX518 or MK4166.

According to the invention there is also provided a therapeutic combination comprising:
  a. an immune checkpoint blockade agent, and
  b. a therapeutic agent that is active in conjunction with immune checkpoint blockade to enhance or repress a patient's response associated with a malignant condition.

According to a preferred form of the invention the therapeutic agent is selected according to the method of the invention. Preferably the therapeutic agent is identified by:
  a. receiving a target set of genetic materials from a plurality of animals, each either responding or non-responding to immunotherapy of a cancer condition;
  b. evaluating and searching for gene pairs that are expressed in a correlated fashion (positive or negative) over many samples in a dataset;
  c. identifying dependency network structures for the plurality of genes for each condition;
  d. defining genetic modules and or hubs that serve as an intervention point in treatment efficacy;
  e. interrogating publicly available databases of drug-treated cell lines with module or hub data derived from step (d); and
  f. identifying at least a therapeutic agent that either (i) influences a response (positive or negative) associated with at least a module that governs and or dominates a response to immune checkpoint blockade from animals that respond to a treatment.

According to the invention step (f) in the above method may be achieved by interrogating publicly available drug databases and the biomedical literature to identify drugs that are capable of influencing the biological activity of at least a module or hub that is pivotal to the genetic activity and or equilibrium of a malignant condition.

The immune checkpoint blockade agent that is used in the therapeutic composition is preferably selected from:
   a. an agent that targets the inhibitory T cell molecule CTLA-4 eg a CTLA-4 antagonist (such as ipilimumab or tremelimumab);
   b. an agent that targets PD-1 eg a PD-1 antagonist (such as nivolumab, AMP-224, pidilizumab or pembrolizumab);
   c. an agent that targets PD-L1 eg a PD-L1 antagonist (such as MPDL-3280A, MSB0010718C or MEDI4736); or
   d. a glucocorticoid-induced TNFR family related gene (GITR) member (such as TRX518 or MK4166).

In a specific form of the invention the CTLA-4 antagonist used in the therapeutic compositions of the invention is ipilimumab or tremelimumab.

In a specific form of the invention the PD-1 antagonists used in the therapeutic composition of the invention is nivolumab, AMP-224, pidilizumab or pembrolizumab.

In a specific form of the invention the PD-L1 antagonists used in the therapeutic compositions of the invention is MPDL-3280A, MSB0010718C or MEDI4736.

When the immune checkpoint blockade agent is an anti-CTLA-4 agonist or a glucocorticoid-induced TNFR family related gene (GITR) member, the therapeutic agent preferably targets the following molecules or their biological activity: NOS2 (iNOS), Aurora kinase B, Ect2, Rho kinases or retinoid receptors. More preferably the therapeutic agent is selected from one or a combination of the following agents: Isosorbide dinitrate (ISDN), Isosorbide dinitrate, JS-K, isosorbide mononitrate or nitroclycerin; All-trans-retinoid acid (ATRA); VX-680 (aurora kinase inhibitor); Meticrane; Hydrocotamine; Fasudil (Rho kinase inhibitor); Galantamine; Pyridoxine (vitamin B6); flavopiridol.

According to one of the embodiments, the invention provides for the treatment of a patient with a malignant condition by administering to said patient a combination of at least an immune checkpoint blockade agent and the therapeutic agent. Preferably said method employs a therapeutic composition as described herein.

In an alternate embodiment the invention resides in a method of treating a patient with a malignant condition, said method comprising the steps of:
   a. identifying one or more therapeutic agents that work in a coordinated manner with immune checkpoint blockade agents to phenocopy a network of responding tumours;
   b. administering to said patient a combination of at least an immune checkpoint blockade agent and the therapeutic agent wherein said therapeutic agent (a) phenocopies a module of a genetic network associated with a responding malignant condition or (b) influence the biological activity of a genetic hub that is pivotal to the genetic activity and or equilibrium of a malignant condition.

The administration may occur concurrently, sequentially, or alternately. Concurrent administration refers to administration of the therapeutic agent and the immune checkpoint blockade agent at essentially the same time. For concurrent co-administration, the courses of treatment may also be run simultaneously. For example, a single, combined formulation of the agents may be administered to the patient.

Additional objectives, advantages and novel features will be set forth in the description which follows or will become apparent to those skilled in the art upon examination of the drawings and the ensuing detailed description of several non-limiting embodiments which follows.

REFERENCE TO COLOR FIGURES

This application contains at least one illustration executed in color. Copies of this patent application publication with color illustrations will be provided by the Office upon request and payment of the necessary fee.

BRIEF DESCRIPTION OF THE DRAWINGS

The disclosure will provide details in the following description of preferred embodiments with reference to the following figures wherein.

DETAILED DESCRIPTION OF THE INVENTION

Figure 1:
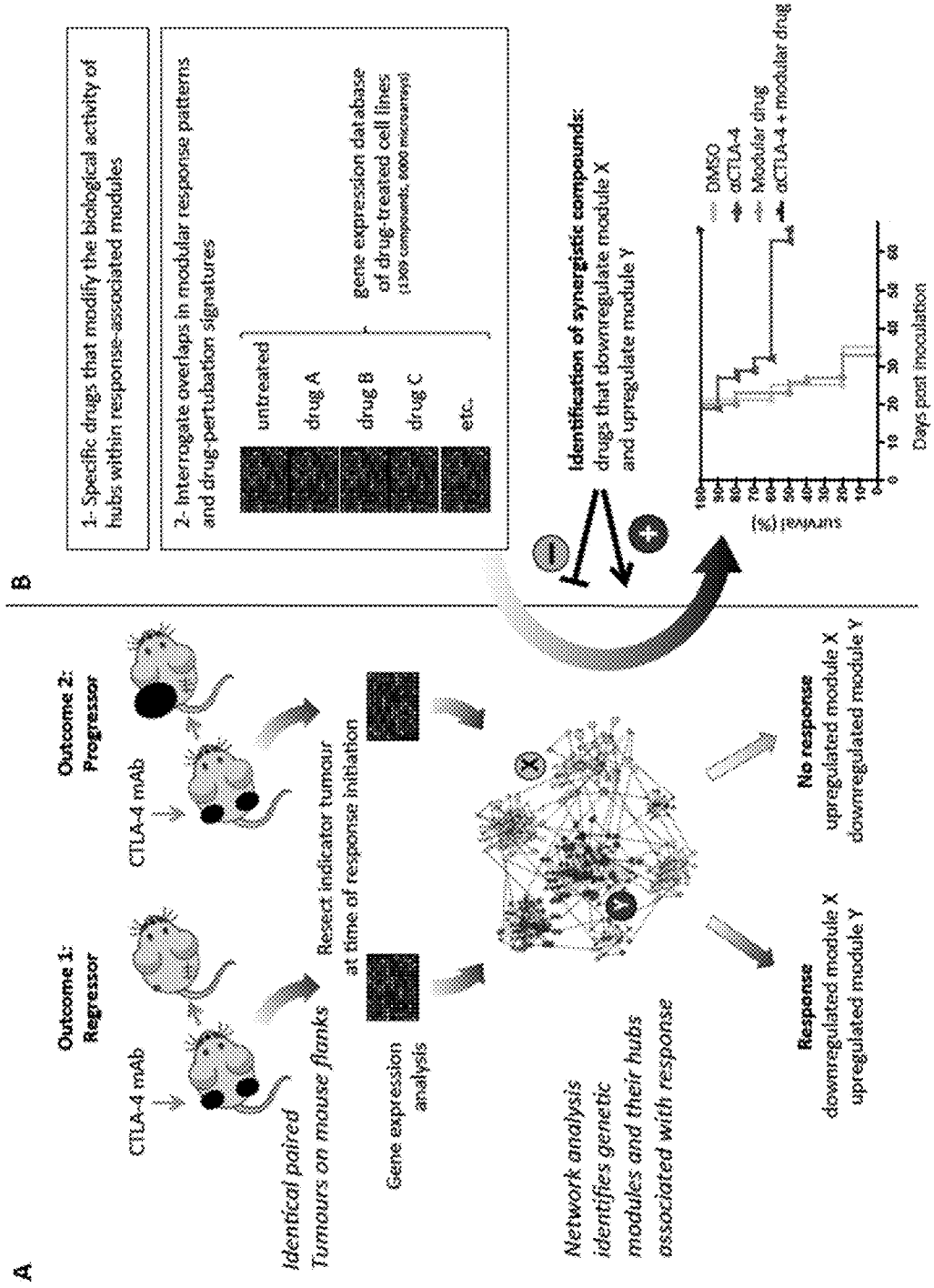
FIG. 1 presents a schematic of the experimental approach used herein.

The present invention is founded on an investigation of the molecular mechanisms of regressing cancer following immunotherapy and seeks to pharmacologically reinforce those events to improve the efficacy of current treatments.

The present invention is not to be limited in scope by the following specific embodiments. This detailed description is intended for the purpose of exemplification only. Functionally equivalent products, compositions and methods are within the scope of the invention as described herein. Consistent with this position, those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively and any and all combinations or any two or more of the steps or features.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

Throughout this specification, unless the context requires otherwise, the word "comprise", or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

The invention described herein may include one or more range of values (for example, size, displacement and field strength etc.). A range of values will be understood to include all values within the range, including the values defining the range, and values adjacent to the range that lead to the same or substantially the same outcome as the values immediately adjacent to that value which defines the boundary to the range. For example, a person skilled in the field will understand that a 10% variation in upper or lower limits of a range can be totally appropriate and is encompassed by the invention. More particularly, the variation in upper or lower limits of a range will be 5% or as is commonly recognised in the art, whichever is greater.

Throughout this specification relative language such as the words 'about' and 'approximately' are used. This language seeks to incorporate at least 10% variability to the specified number or range. That variability may be plus 10% or negative 10% of the particular number specified.

As described herein the present invention relates to the discovery of signatures of coordinately expressed genes and gene networks associated with an individuals response to a malignant condition and to methods for identifying and using compounds that regulate and in some cases recalibrate gene sets and gene pathways associated with cancer wherein such regulation and recalibration effectively halt or reverse the effects of the condition.

In some embodiments the invention provide a computer-implemented method for identifying or evaluating relationships between gene molecular interaction networks to identify genetic modules and hubs that govern the response to immune checkpoint blockade from animals that respond to a cancer treatment.

As used herein a module is a genetic network (such as that illustrated by a gene fingerprint or picture) formed of a plurality of genetic hubs or genes that are broadly either upregulated or down regulated and which are associated with growth (be it increasing or decreasing growth) of a malignancy in an animal responding to or non-responding to immunotherapy of a malignant condition. For example a module may represent all those genes that are upregulated or down regulated and which are associated with growth of a malignancy. Alternatively, a module might represent all the genes that are upregulated or downregulated in the immune response associated with the growth of a malignancy.

As used herein a hub is an isolated gene or a select number of genes that are pivotal to the genetic activity and or equilibrium of a malignant condition in an animal responding to or non-responding to immunotherapy for that malignant condition.

In one embodiment, the computer-implemented method comprises the steps of:
a. receiving a target set of genetic materials from a plurality of animals each either responding or non-responding to immunotherapy of a cancer condition;
b. evaluating and searching for gene pairs that are expressed in a correlated fashion (positive or negative) over many samples in a dataset;
c. identifying dependency network structures for the plurality of genes for each condition; and
d. defining modules and more specifically hubs that serve as an intervention point in treatment efficacy.

In accordance with the present invention a range of immunotherapies may be examined using the method of the invention. Preferably, the immunotherapy is one that blocks an immune checkpoint or that influences and immune checkpoint. Such a blockade refers to a plethora of inhibitory pathways hardwired into the immune system that maintain self-tolerance and modulate the duration and amplitude of physiological immune responses in order to minimize collateral tissue damage.

In accordance with a further aspect of this embodiment of the invention there is provided a method that further comprising the steps of:
a. interrogating publicly available databases of drug-treated cell lines with module data derived from the method described above; and
b. selecting those therapeutic agents that influence a response (positive or negative) associated with at least a module that governs and or dominates a response to immunotherapy by animals that respond to a treatment.

In accordance with an alternate aspect of this embodiment of the invention there is provided a method that further comprising the steps of:
a. interrogating publicly available drug databases with hub data derived from the method described above; and
b. selecting at least a therapeutic agents that is capable of influencing the biological activity of a hub that is pivotal to the genetic activity and or equilibrium of a malignant condition.

Tumours co-opt certain immune-checkpoint pathways as a major mechanism of immune resistance, particularly against T cells that are specific for tumour antigens. Preferably, the immune checkpoint pathway that is blocked in the method of the present invention is that associated with one or more of the following targets: cytotoxic T-lymphocyte-associated antigen 4 (CTLA4), programmed cell death protein 1 (PD1), PD1 ligand, GITR, T cell membrane protein 3, LAG3, lymphocyte activation gene 3, B7-H3 or B7-H4.

In a highly preferred form of the invention the blocked immune checkpoint pathway is associated with one or more (a combination) of the following targets: CTLA4, PD1, PD1 ligand or GITR. For example, the immunotherapy is selected from agents that target (a) CTLA-4 such as ipilimumab or tremelimumab; (b) PD-1 such as nivolumab, pidilizumab or pembrolizumab, AMP-224; (c) PD-L1 such as MPDL-3280A, MSB0010718C or MEDI4736; or (d) GITR such as TRX518 or MK4166. To improve on the number of patients who benefit from immune checkpoint blockade, CTLA-4, PD-1, PD-L1 and or GITR antibodies are combined in a preferred form of the invention. Details of these products, their targets and the cancer types that they are primarily used against are provided in the following Table 1.

TABLE 1

Antibodies targeting CTLA-4, PD-1 or its ligand PD-L1

| Antibody | Target | Company | Cancer Types |
| --- | --- | --- | --- |
| ipilimumab | CTLA-4 | BMS | melanoma lung/prostate many other cancers |
| tremelimumab | CTLA-4 | Pfizer | mesothelioma lung/melanoma (with other drugs) |
| nivolumab | PD-1 | BMS | melanoma/lung/kidney many other cancers |
| pembrolizumab | PD-1 | Merck | melanoma/lung many other cancers |
| MPDL-3280A | PD-L1 | Roche | melanoma/lung kidney and many other cancers |
| MEDI4736 | PD-L1 | AstraZeneca | lung |
| AMP-224 | PD-1 | | melanoma/lung kidney and many other cancers |
| MSB0010718C | PD-L1 | EMD-Serono | melanoma/lung kidney and many other cancers |

TABLE 1-continued

Antibodies targeting CTLA-4, PD-1 or its ligand PD-L1

| Antibody | Target | Company | Cancer Types |
| --- | --- | --- | --- |
| pidilizumab | PD-1 | Cure Tech | lymphoma/brain |
| TRX518 | GITR | GITR Inc. | melanoma many other cancers |
| MK4166 | GITR | Merck | melanoma many other cancers |

In yet another aspect of the invention, the method is a computerized or computer implemented method for identifying therapeutic intervention points for a malignant condition that is influenced by an immunotherapy, said method comprising:
a. receiving, at a first processor, a set of genetic treatment data from a malignant biological system that responds to an immunotherapy, wherein the data set is derived from a plurality of biological entities;
b. receiving, at a second processor, a set of genetic treatment data from a malignant biological system that fails to fully respond to an immunotherapy, wherein the data set is derived from a plurality of biological entities;
c. providing, at a third processor, a computational network model that represents the malignant biological system and includes nodes and modules that represent gene pairs that are expressed in a correlated fashion (positive or negative) over a plurality of samples;
d. calculating, with a fourth processor, activity measures and or co-expression relationships, for the nodes, representing dependency network structures for the plurality of genes expressed in the non or partially responding data sets and the responding data sets;
e. identifying with a fifth processor, the genetic modules and more specifically the hubs that govern and or dominate a response to immune checkpoint blockade from animals that respond to a treatment.

In a preferred form of the above method the data generated by the fifth processor is then used by a sixth processor to interrogate publicly available databases identify drugs that influence a response (positive or negative) associated with at least a module or hub that governs and or dominates a response to immune checkpoint blockade from animals that respond to a treatment.

Using this method of the invention it is possible to identify drugs that work in a coordinated manner with immune checkpoint blockade agents to phenocopy a network in responding tumours.

In a second embodiment, the invention provides a system to identify drugs that work in a coordinated manner with immune checkpoint blockade agents to phenocopy a network module of responding tumours, said method comprising the steps of:
a. interrogating with module data derived from the above method for therapeutic agent(s) that influence a response associated with at least a module or hub that governs and or dominates a response to immune checkpoint blockade from animals that respond to a treatment.

When the above method is employed in the analysis of mesothelioma and the immunotherapeutic agent target CTLA-4, an expression pattern of a response associated module is generated.

A therapeutic agent that can influence a response in a module is a therapeutic agent that works in concert with an immune checkpoint modulating agent to either positively up regulate or negatively down regulate the activity of the module or hub under consideration. This may be achieved by the therapeutic agent having a biological effect on either a single gene in the module or hub or by having a biological effect on one or more genes that make up the module or hub.

When the module data are compared to publicly available databases of drug-treated cell lines the following drugs, listed in table 2, were identified as agents that work in concert with an antiCTLA-4 agent to influence a module response (positive or negative) associated with mesothelioma.

TABLE 2

List of repurposed therapeutic agents that phenocopy the expression pattern of the response associated modules

| Drug | Class | Original indication |
|---|---|---|
| all-trans retinoic acid | retinoic acid derivative | Acne skin disease and as stem cell differentiation inducer in promyelocytic leukemia |
| Meticrane | Thiazide diuretics | Hypertension |
| Pyridoxine | Vitamine B6 | Vitamine B6 deficiency and to prevent side-effects from anti-tuberculosis drugs |
| Galantamine | | Alzheimers Disease |
| Bexarotene | retinoic acid derivative | in trials: cancer, cushing's disease, alzheimer |
| CD1530 | retinoic acid receptor-γ agonist | in development (cancer) |
| SR11237 | pan-retinoic acid receptor agonist | in development (cancer) |
| Ro 41-5253 | retinoic acid receptor-α agonist | in development (cancer) |
| Gabapentin | γ-aminobutyric acid mimetic | Epilepsy and neuropathic pain |
| trioxysalen | psoralen derivative | photosensitisation in combination with UV light in skin diseases |
| Calcitriol | Active form of Vitamin D | Osteoporosis and hypocalcemia |
| cetirizine | antihistamine | Allergies |

In accordance with this form of the invention there is provided a therapeutic combinations that comprise at least a therapeutic agent that is active in conjunction with immune checkpoint blockade to enhance or repress a patient's response associated with a malignant condition.

Preferably, the immune checkpoint blockade agent targets or works in association with the inhibitory T cell molecule CTLA-4 and or targets the Programmed Death receptor (PD-1) or its ligands or Agents that target GITR. For example, an agent that targets the inhibitory T cell molecule CTLA-4 is a CTLA-4 antagonist such as ipilimumab or tremelimumab. An agent that targets PD-1 is a PD-1 antagonist such as nivolumab, AMP-224, pidilizumab or pembrolizumab. An agent that targets PD-L1 is a PD-L1 antagonist such as MPDL-3280A, MSB0010718C or MEDI4736. Agents that target GITR are GITR antagonists such as TRX518 or MK4166.

When the immune check point blocking agent is the inhibitory T cell molecule CTLA-4 the therapeutic agent is selected from one or more of the following classes of drug: retinoic acid derivatives, Thiazide diuretics, Vitamin B6, retinoic acid receptor-γ agonists, pan-retinoic acid receptor agonists, retinoic acid, receptor-α agonist, γ-aminobutyric acid mimetics, psoralen derivatives, Active forms of Vitamin D and its derivatives orantihistamines.

In a highly preferred form of the invention the therapeutic agent is selected from the group comprising: all-trans retinoic acid, Meticrane, Pyridoxine, Galantamine Bexarotene, CD1530, SR11237, Ro 41-5253, Gabapentin, trioxysalen, Calcitriol, cetirizine or funcational derivatives thereof.

In a third embodiment, the invention provides a system to identify drugs that work in a coordinated manner with immune checkpoint blockade agents to phenocopy a network hub in a responding tumours, said method comprising the steps of:

a. receiving a target set of genetic materials from a plurality of animals each either responding or non-responding to immunotherapy of a cancer condition;

b. evaluating and searching for gene pairs that are expressed in a correlated fashion (positive or negative) over many samples in a dataset;

c. identifying dependency network structures for the plurality of genes for each condition;

d. defining modules and more specifically hubs that serve as an intervention point in treatment efficacy;

e. selecting a hub that influence the genetic activity and or equilibrium of a malignant condition; and f. interrogating publicly available drug databases to identify at least a drug that is capable of upregulating or down regulating the hub.

When the above method is employed in the analysis of mesothelioma and the immunotherapeutic agent target CTLA-4, a number of hubs have been identified that will act in combination with the immune blockade agent to influence an animals response to a mesothelioma. In particular, the hubs can be functionally categorized or broken into subclasses as follows in Table 3.

TABLE 3

Classification of hubs into functional categories

| Functional category/subclass | # | Hub |
|---|---|---|
| 1 cell adhesion molecule (PC00069) | 9 | CD2, CD81, CDH2, ITGA4, ITGAV, ITGB2, LGALS3, PECAM1, SELL |
| 2 chaperone (PC00072) | 1 | CCT5 |
| 3 defense/immunity protein (PC00090) | 14 | ADIPOQ, C3, CD3E, CD4, CD8a, CD86, FCER1G, FCGR2A, FCGR2B, H2-Aa, H2-ab1, H2-eb1, IFNGR1, PTX3 |
| 4 enzyme modulator (PC00095) | 5 | CAV1, CCNA2, CCND1, PIK3R1, RAN |
| 5 hydrolase (PC00121) | 8 | CD38, FAS, FASN, LPL, PTPRC, PTPRJ, SH2D1A, TNFAIP3 |
| 6 kinase (PC00137) | 12 | AURKA, AURKB, BUB1B, CDK1, CHEK1, ITK, JAK2, MET, PIK3CG, PRKCA, PRKCQ, RIOK2 |
| 7 ligase (PC00142) | 2 | ACACA, CBLB |
| 8 nucleic acid binding (PC00171) | 8 | HDAC2, HNRNPH1, MCM6, PARP1, SUV39H1, WHSC1, XRCC5, ZFP36 |
| 9 oxidoreductase (PC00176) | 4 | CYBB, HMOX1, NOS2, SOD2 |
| 10 metabolic process (GO:0008152) | 3 | FABP4, MAD2L1, SAMSN1 |
| 11 protease (PC00190) | 5 | DPP4, MMP3, MMP9, MMP12, MMP13 |
| 12 receptor (PC00197) | 7 | CCR2, CD36, CXCR2, CXCR3, IL2RA, TNFRSF9, XPO1 |
| 13 signaling molecule (PC00207) | 25 | APOE, CCL2, CCL3, CCL5, CCL22, CD28, CTLA-4, CXCL3, CXCL9, ECT2, FYB, ICOS, IFNG, IGF1, IL1A, IL-1B, IL1RN, IL33, INHBA, INSIG1, IRS1, LAT, LCP2, PF4, S100A9 |

TABLE 3-continued

Classification of hubs into functional categories

| Functional category/subclass | # | Hub |
|---|---|---|
| 14 transcription factor (PC00218) | 11 | CTTN, EGR2, ELAVL1, FOXM1, HIF1A, IKZF1, RBL1, REL, SATB1, STAT4, TWIST1 |
| 15 transporter (PC00227) | 1 | ABCA1 |

The above hubs were classified according to functional categories derived from the PANTHER protein class (PC) system. Hubs that were not classified by PANTHER were manually curated into relevant PANTHER classes or assigned to gene ontology (GO) functional categories.

When the above hubs were interrogated against publicly available drug databases the inventors identified at least the following drugs, identified in Table 4, that are capable of upregulating or down regulating the particular hubs listed.

TABLE 4

List of hubs with respective specific agents

| hub | Module | up or downregulated in responders | drug name | class |
|---|---|---|---|---|
| NOS2 (iNOS) | Cancer | Up | isosorbide dinitrate | NO generator |
| | | | isosorbide mononitrate | NO generator |
| | | | nitroglycerin | NO generator |
| | | | JS-K | NO generator |
| Aurora kinase B | Cancer | Down | VX680 | Aurora kinase inhibitor |
| Ect2 | Cancer | Down | Fasudil | Rho Kinase inhibitor |
| CDKN1 | Cancer | Down | Flavopiridol | cyclin-dependent kinase inhibitor |

Note:
JS-K is an experimental agent that has been used in vitro and in animal models in cancer.

The present invention further relates to therapeutic combinations that comprise at least a therapeutic agent that is active in conjunction with immune checkpoint blockade to enhance or repress a patient's response associated with a malignant condition.

Preferably, the immune checkpoint blockade agent targets the inhibitory T cell molecule CTLA-4 and or targets the Programmed Death receptor (PD-1) or its ligands. For example, an agent that targets the inhibitory T cell molecule CTLA-4 is a CTLA-4 antagonist such as ipilimumab or tremelimumab. An agent that targets PD-1 is a PD-1 antagonist such as nivolumab, AMP-224, pidilizumab or pembrolizumab. An agent that targets PD-L1 is a PD-L1 antagonist such as MPDL-3280A, MSB0010718C or MEDI4736.

Preferably the therapeutic agent and the immune checkpoint blockade function in a synergistic manner. A synergistic effect refers to a greater-than-additive effect that is produced by the combination being examined.

According to a preferred form of the invention the therapeutic agent is selected according to the method of the invention. Preferably the therapeutic agent is identified by:
   a. receiving a target set of genetic materials from a plurality of animals, each either responding or non-responding to immunotherapy of a cancer condition;
   b. evaluating and searching for gene pairs that are expressed in a correlated fashion (positive or negative) over many samples in a dataset;
   c. identifying dependency network structures for the plurality of genes for each condition;
   d. defining genetic modules and or hubs that serve as an intervention point in treatment efficacy;
   e. interrogating publicly available databases of drug-treated cell lines with module or hub data derived from step (d); and
   f. identifying at least a therapeutic agent that either (i) influences a response (positive or negative) associated with at least a module that governs and or dominates a response to immune checkpoint blockade from animals that respond to a treatment.

According to the invention step (f) in the above method may be achieved by interrogating publicly available drug databases and the biomedical literature to identify drugs that are capable of influencing the biological activity of at least a module or hub that is pivotal to the genetic activity and or equilibrium of a malignant condition.

The immune checkpoint modulating agent that is used in the therapeutic composition is preferably selected from:
   a. an agent that targets the inhibitory T cell molecule CTLA-4 e.g. a CTLA-4 antagonist (such as ipilimumab or tremelimumab);
   b. an agent that targets PD-1 e.g. a PD-1 antagonist (such as nivolumab, AMP-224, pidilizumab or pembrolizumab);
   c. an agent that targets PD-L1 e.g. a PD-L1 antagonist (such as MPDL-3280A, MSB0010718C or MEDI4736); or
   d. a glucocorticoid-induced TNFR family related gene (GITR) member (such as TRX518 or MK4166).

In a specific form of the invention the CTLA-4 antagonist used in the therapeutic compositions of the invention is ipilimumab or tremelimumab.

In a specific form of the invention the PD-1 antagonists used in the therapeutic composition of the invention is nivolumab, AMP-224, pidilizumab or pembrolizumab.

In a specific form of the invention the PD-L1 antagonists used in the therapeutic compositions of the invention is MPDL-3280A, MSB0010718C or MEDI4736.

When the immune checkpoint modulating agent is an anti-CTLA-4 agonist or a glucocorticoid-induced TNFR family related gene (GITR) member, the therapeutic agent is preferably NOS2 (iNOS), Aurora kinase B, Ect2 or IGF1. More preferably the therapeutic agent is selected from one or a combination of the following agents: Isosorbide dinitrate (ISDN), Isosorbide dinitrate, JS-K, isosorbide mononitrate or nitroclycerin; All-trans-retinoid acid (ATRA); VX-680 (aurora kinase inhibitor); Meticrane; Hydrocotamine; Fasudil (Rho kinase inhibitor); Galantamine; Pyridoxine (vitamin B6); flavopiridol.

According to an embodiment, the invention also provides for the treatment of a patient with a malignant condition, said method comprising the step of administering to said patient a combination of at least an immune checkpoint blockade agent and the therapeutic agent.

In an alternate form the invention resides in a method of treating a patient with a malignant condition, said method comprising the steps of:
   a. identifying one or more therapeutic agents that work in a coordinated manner with immune checkpoint modulating agents to phenocopy a network of responding tumours, using a method of the invention described above; and b. administering to said patient a combination of at least an immune checkpoint modulating agent and the therapeutic agent (identified in step (a)).

Preferably step a in the above method of treatment is used to identify a therapeutic agent that (a) phenocopies a module of a genetic network associated with a responding malignant condition or (b) influence the biological activity of a genetic hub that is pivotal to the genetic activity and or equilibrium of a malignant condition.

Preferably the method of treatment is for mesothelioma, lung cancer cells, or kidney cancer cells. Most preferably the immune checkpoint modulating agent is an anti-CTLA-4 agonist.

Administration of the combination may occur concurrently, sequentially, or alternately. Concurrent administration refers to administration of the therapeutic agent and the immune checkpoint blockade agent at essentially the same time. For concurrent co-administration, the courses of treatment may also be run simultaneously. For example, a single, combined formulation of the agents may be administered to the patient.

In the method of the present invention, the therapeutic agent and immune checkpoint blockade agent may be administered in separate, individual treatments that are spaced out over a period of time, so as to obtain the maximum efficacy of the combination. When spaced out over a period of time, a patient is preferably given one treatment for a period of time (say 1 to 10 days, preferably about 3 to 5 days) following which the second agent is then administered to the patient. This cycle may be repeated as manner times as necessary and as long as the patient is capable of receiving said treatment.

As used herein "treatment" includes:
(i) preventing a disease, disorder or condition from occurring in an subject which may be predisposed to the disease, disorder and/or condition but has not yet been diagnosed as having it;
(ii) inhibiting the disease, disorder or condition, i.e., arresting its development; or
(iii) relieving the disease, disorder or condition, i.e., causing regression of the disease, disorder and/or condition.

According to the invention the patient to be treated is preferably a mammal (e.g., a human, companion animal, or commercial animal, including cows, dogs, monkeys, mice, pigs, and rats). Most preferably it is a human.

In the method of the present invention, an amount of active agent that is administered to the patient to treat the malignant condition is an amount that is effective to ameliorate or minimize the clinical impairment or symptoms of the condition, in either a single or multiple dose form. For example, the clinical impairment of symptoms of a malignant condition may be ameliorated or minimized by diminishing any pain or discomfort suffered by the subject; by extending the survival of the subject beyond that which would otherwise be expected in the absence of such treatment; by inhibiting or preventing the development or spread of the condition; or by limiting, suspending, terminating, or otherwise controlling the maturation and proliferation of cells in the condition. Notably, the amounts of the agents effective to treat a malignant condition in a subject in need of treatment will vary depending on the type of agent used, as well as the particular factors of each case, including the type of condition, the stage of the condition, the subject's weight, the severity of the subject's condition, and the method of administration. These amounts can be readily determined by the skilled artisan.

The therapeutic combination described herein may be administered to a subject by known procedures, including, but not limited to, oral administration, parenteral administration (e.g., intramuscular, intraperitoneal, intravascular, intravenous, or subcutaneous administration), and transdermal administration.

The formulations may be presented in unit or multi-dose containers, such as sealed ampoules or vials. Moreover, the formulations may be delivered by any mode of injection, including, without limitation, epifascial, intracapsular, intracutaneous, intramuscular, intraorbital, intraperitoneal (particularly in the case of localized regional therapies), intraspinal, intrasternal, intravascular, intravenous, parenchymatous, or subcutaneous.

In an embodiment the invention provides for the treatment of a patient with a malignant condition by administering to said patient a therapeutic combination of at least an immune checkpoint blockade agent and the therapeutic agent. Preferably, the therapeutic combination provides a treatment of mesothelioma.

Where such a mesothelioma treatment is provided the therapeutic agent is a nitric oxide (NO) generator that is combined with the immune checkpoint blockade agent. For example, when the immune checkpoint blockade agent is anti-CTLA4 and the NO generator is selected from isosorbide dinitrate (ISDN) and JS-K.

Where such a mesothelioma treatment is provided the therapeutic agent is a retinoid retinoid that is combined with the immune checkpoint blockade agent. For example, when the immune checkpoint blockade agent is anti-CTLA4 and the retinoid is All-trans retinoic acid (ATRA).

In an alternate example of the invention when the immune checkpoint blockade agent is glucocorticoid-induced TNFR family related gene (GITR) the therapeutic agent is selected from ISDN and ATRA.

In an embodiment, the invention provides for the treatment of a patient with a renal cancer by administering to said patient a therapeutic combination of at least an immune checkpoint blockade agent and the therapeutic agent. For example, when the immune checkpoint blockade agent is anti-CTLA4 and the therapeutic agent is selected from ATRA and ISDN.

In an embodiment, the invention provides for the treatment of a patient with a lung cancer by administering to said patient a therapeutic combination of at least an immune checkpoint blockade agent and the therapeutic agent. For example, when the immune checkpoint blockade agent is anti-CTLA4 and the therapeutic agent is ISDN.

Features of the invention will now be discussed with reference to the following non-limiting description and examples.

Further features of the present invention are more fully described in the following Examples. It is to be understood, however, that this detailed description is included solely for the purposes of exemplifying the present invention, and should not be understood in any way as a restriction on the broad description of the invention as set out above.

Examples

The present invention identifies genetic modules that are associated with response to therapeutic blockade of the immune checkpoint Cytotoxic T-Lymphocyte Antigen (CTLA-) 4 and could subsequently pharmacologically negate or amplify the response-associated network, thereby reducing or increasing the therapeutic efficacy of CTLA-4 blockade. In particular, the experiments described herein seek two aims:

Aim #1 Identify in detail the molecular networks that underlie immunotherapy-induced tumour regression.

Aim #2 Identify and validate optimal drug combinations for improving the response rate to immune checkpoint blockade in cancer, which can subsequently be taken to the clinic.

FIG. 1 presents a schematic of the experimental approach used herein—Mice with bilaterally inoculated tumours were treated with anti-CTLA-4. Responses were symmetric in >90% of mice. Seven days after treatment (the 'tipping point'; moment of start of regression), tumours are removed from one side. Based on the growth characteristics of the remaining tumour, the inventors could predict the future reaction to therapy of the already removed tumour. The inventors then performed gene expression analysis (eg microarray or RNAseq analysis) on tumour tissue and constructed a coexpression network, identifying molecular modules, correlating with response. The inventors then used these data to subsequently identify pleiotropic drugs that work in synergy with immune checkpoint blockade by interrogating publically available gene expression databases of drug-treated cell lines for expression signatures that phenocopy the network of responding tumours.

Figure 2:
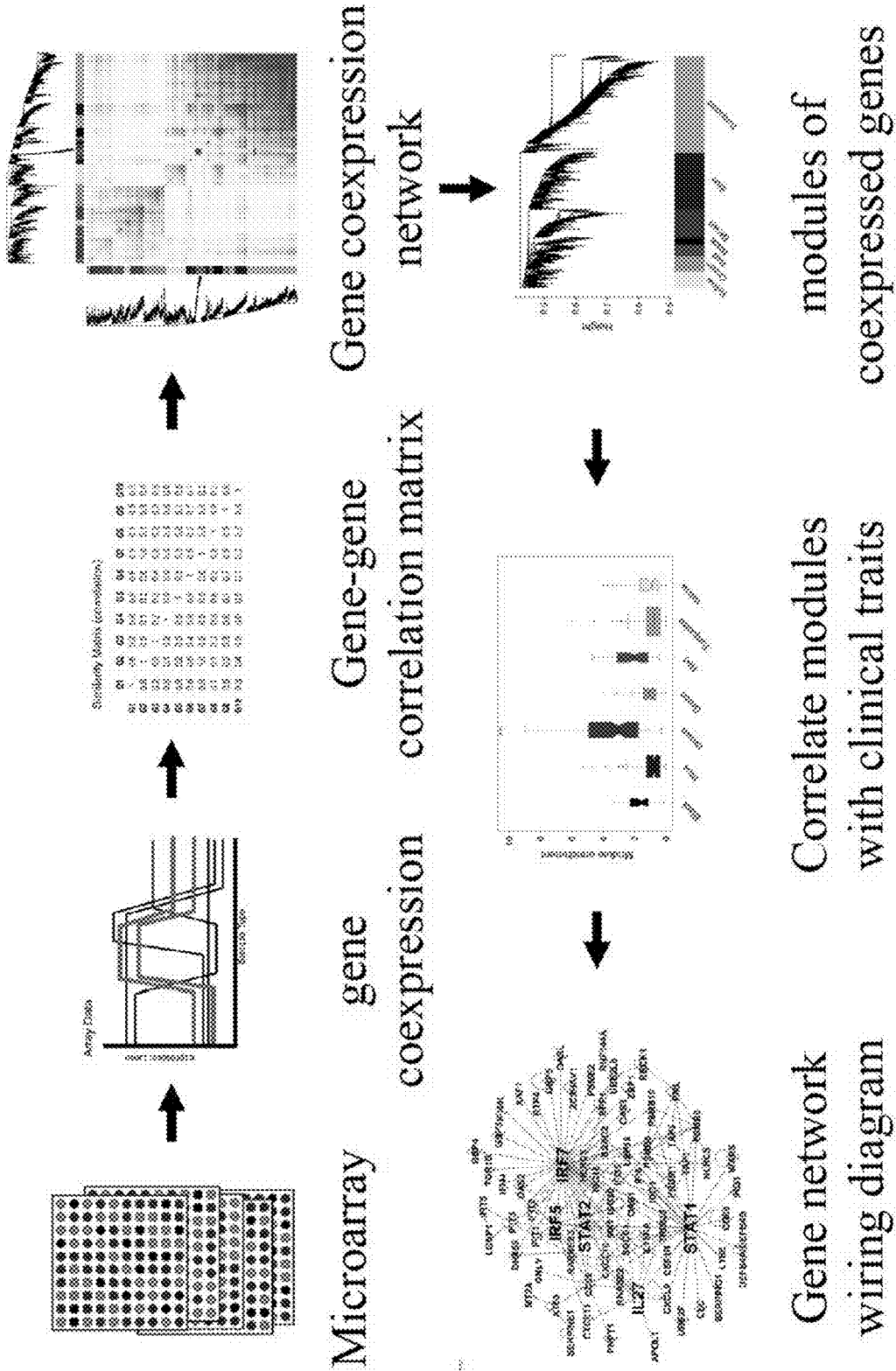
FIG. 2 presents a schematic of reverse network engineering of gene expression data.

FIG. 2 depicts a more detail schematic of how Reverse network engineering of gene expression data is achieved. From gene expression data a coexpression network is constructed by using the weighted gene coexpression network analysis algorithm (WGCNA). The WGCNA algorithm uses a stepwise analytic process that leverages information derived from gene coexpression patterns across the samples to elucidate the global topological structure of the underlying gene networks, thus revealing the modules. The local wiring diagram of selected modules associated with phenotypic traits of interest is reconstructed using functional data from prior studies. Hubs are defined as genes that are involved in at least ten functional interactions with other genes.

The following presents a description of experiments that have been conducted in the development of this invention. At the conclusion of description there are a set of material and methods that are used in the experiments.

The Dual Tumour Model Allows Detailed Assessment of Early Immune Responses in a Responding Versus a Non-Responding Tumour In this experiment mice were inoculated with AB1-HA, and then treated with anti-CTLA-4. Responses were symmetric in >90% of cases (n=55). On day 13 (first evidence of macroscopic response) tumours were surgically removed from one side. Based on the growth characteristics of the remaining tumour, the reaction to therapy of the excised tumour was called. Tumour and lymph node tissue was analyzed by FACS, microarray and immunohisto-chemistry and the data were grouped by responders vs. non-responders.

Figure 3:
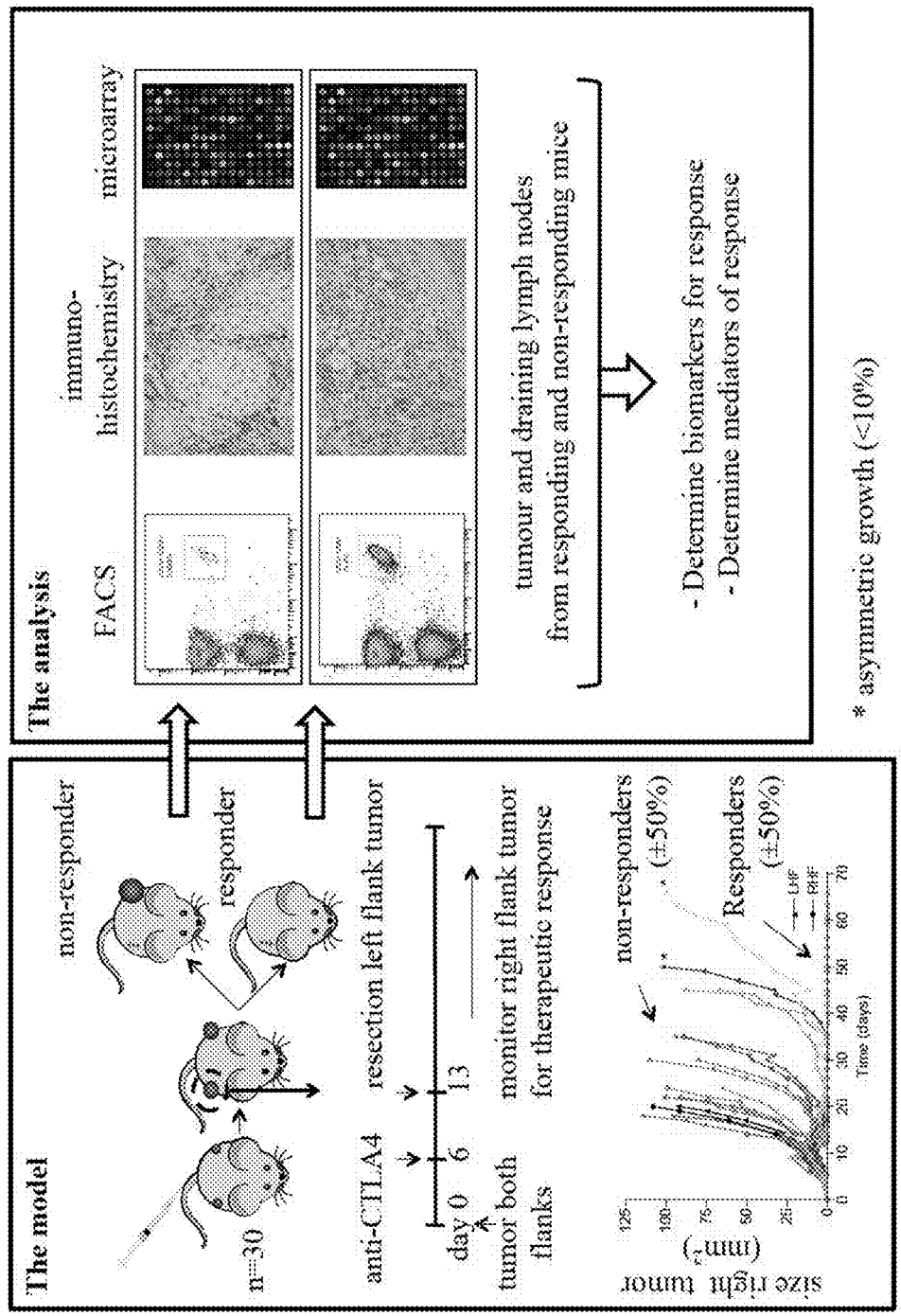
FIG. 3 illustrates that the dual tumour model allows detailed analysis of early events in therapy-responsive versus non-responsive tumours.
Figure 4:
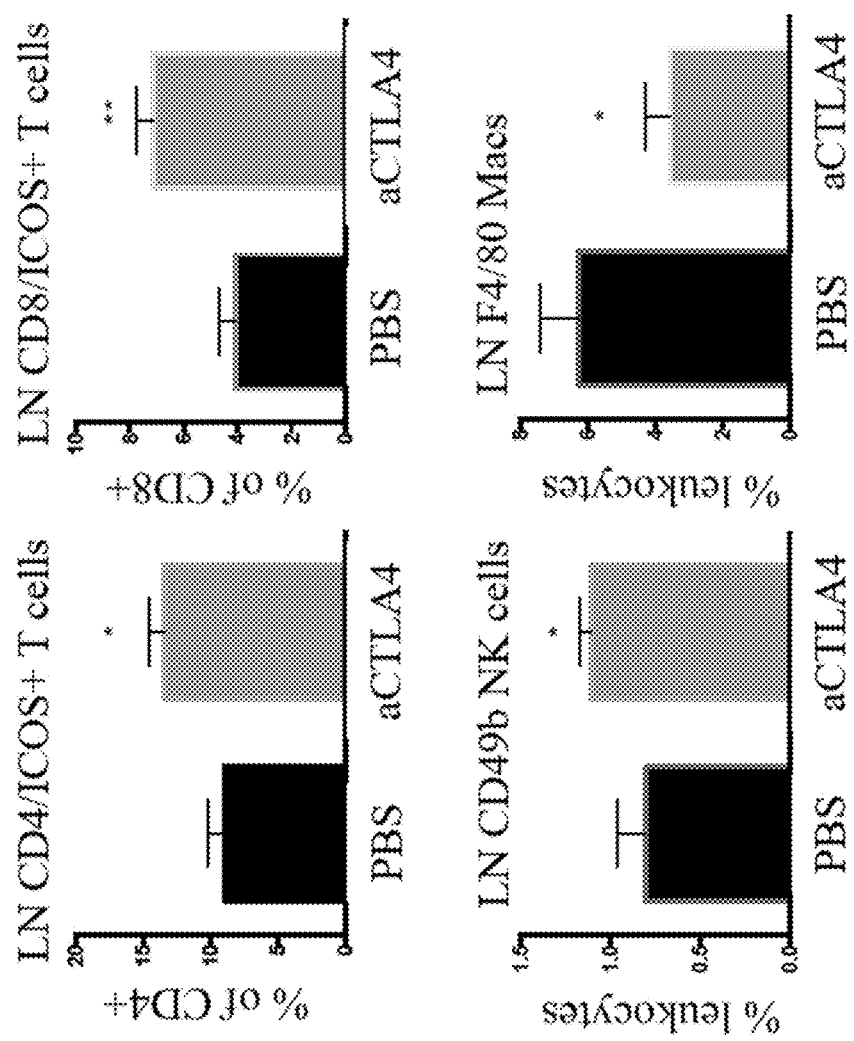
FIG. 4 illustrates that the dual tumour model shows increased frequencies of ICOS+CD4 and CD8 T cells, as well as increased numbers of NK cells in TDLNs of responding mice, while macrophages are decreased in TDLN of responding mice, compared to non-responding mice.

The model allowed the inventors to sample an entire tumour at any given time during treatment, while knowing what the eventual response would have been, by leaving the other flank tumour in situ and monitoring its growth (FIG. 3). The inventors treated mice with anti-CTLA-4 or PBS, surgically removed one of the tumours as well as the tumour-draining lymph node (TDLN) on day 13 at which time regressors and progressors were macroscopically identical. The inventors divided the data into three groups based on the growth of the other tumour that was left in situ; responders, non-responders and untreated. They evaluated ICOS expression by CD4 and CD8 T cells and NK cell numbers in tumour draining lymph nodes, since these have been found to correlate with response to anti-CTLA-4 both in mice and cancer patients. The inventors found that responding mice had significantly more $ICOS^+$ CD4 CD8 and NK cells than non-responding mice, demonstrating the validity of the model (FIG. 4). In addition, they found that macrophage numbers were significantly decreased in responding mice; these cells have been associated with the suppression of effector T cell responses in cancer.

Figure 5A:
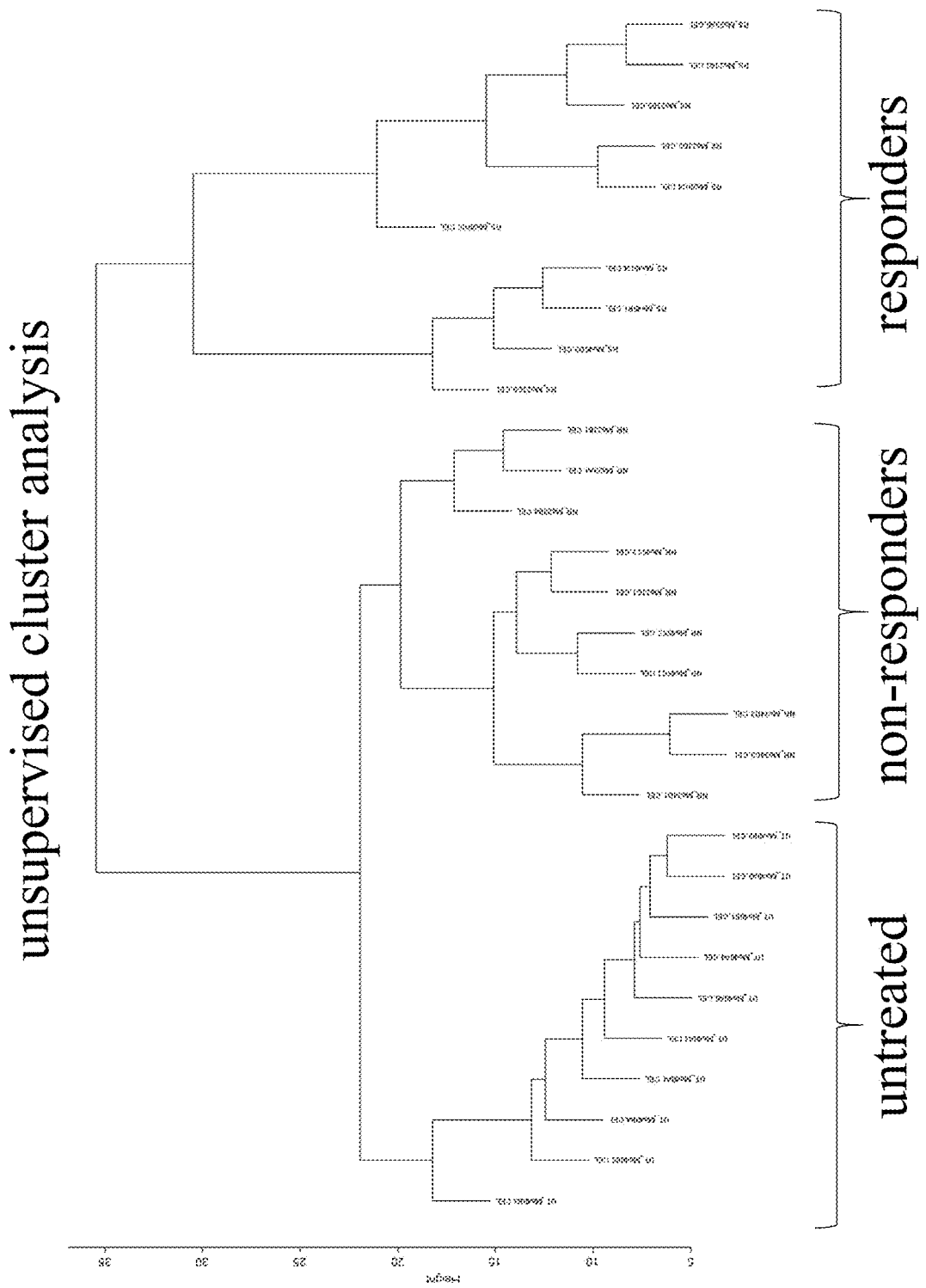
FIG. 5—Gene expression analysis of responding vs non-responding tumours in anti-CTLA-4 treated mice discriminates between response groups and demonstrates a Th1 profile (a) Unsupervised cluster analysis of 30 microarrays obtained from mice that were cured after anti-CTLA-4 (responders; n=10), displayed disease progression (non-responders; n=10) or that were treated with PBS (untreated; n=10). (b) Volcano plot displaying gene significance versus expression ratio, comparing responders and non-responders.
Figure 5B:
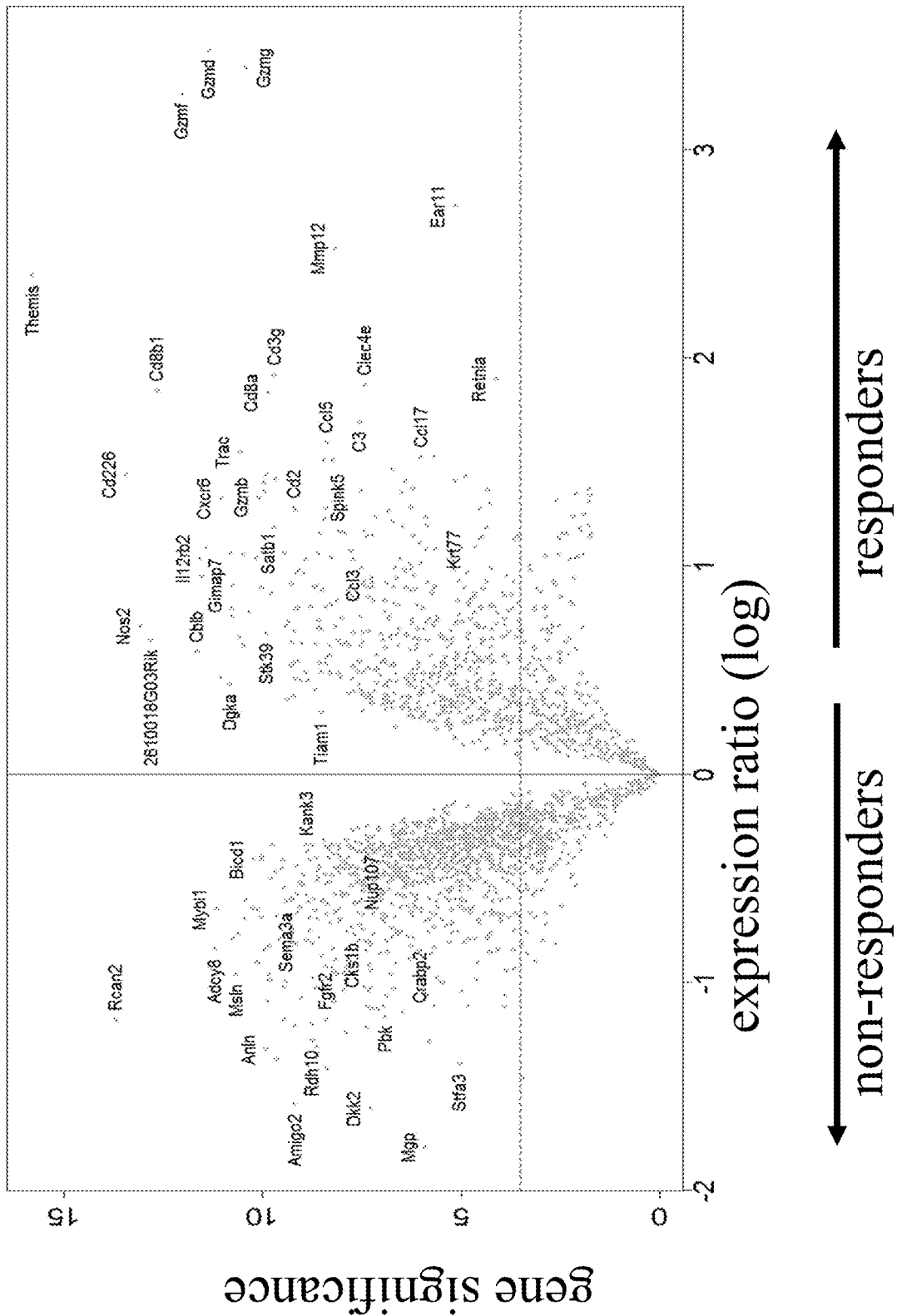
Figure 6A:
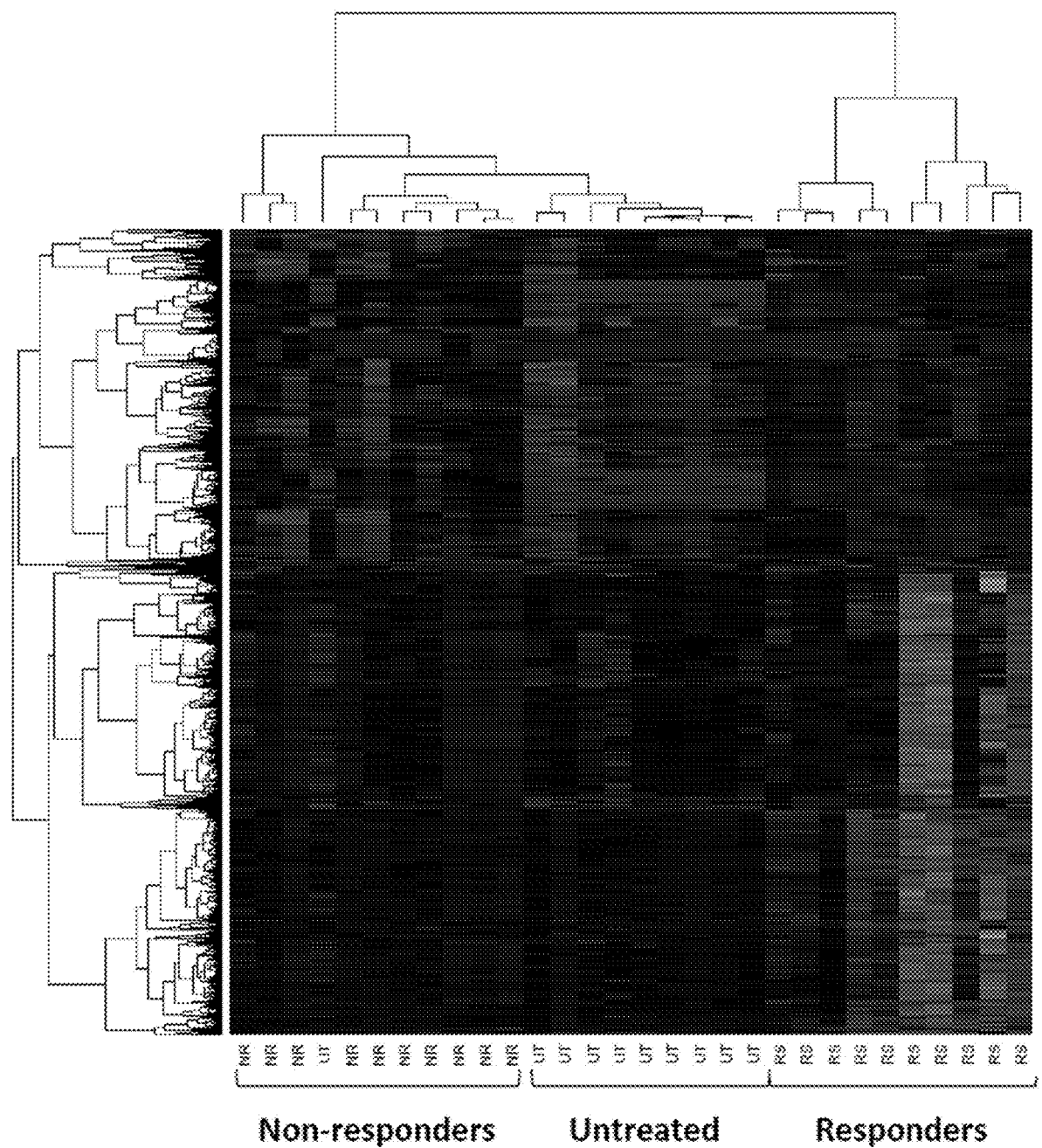
FIG. 6—Identification of response-associated gene networks (A) Unsupervised cluster analysis. (B) WGCNA identified 8 functional modules within the tumour network and (C) comparison of the modules between responders and non-responders showed an up-regulation of the blue module (containing many Th1 immune-related genes) and a down-regulation of the cyan module (containing many cancer-related genes). Prior knowledge based (Ingenuity Systems) reconstruction of the wiring diagram of the modules identified a series of hub genes (D and E)
Figure 6B:
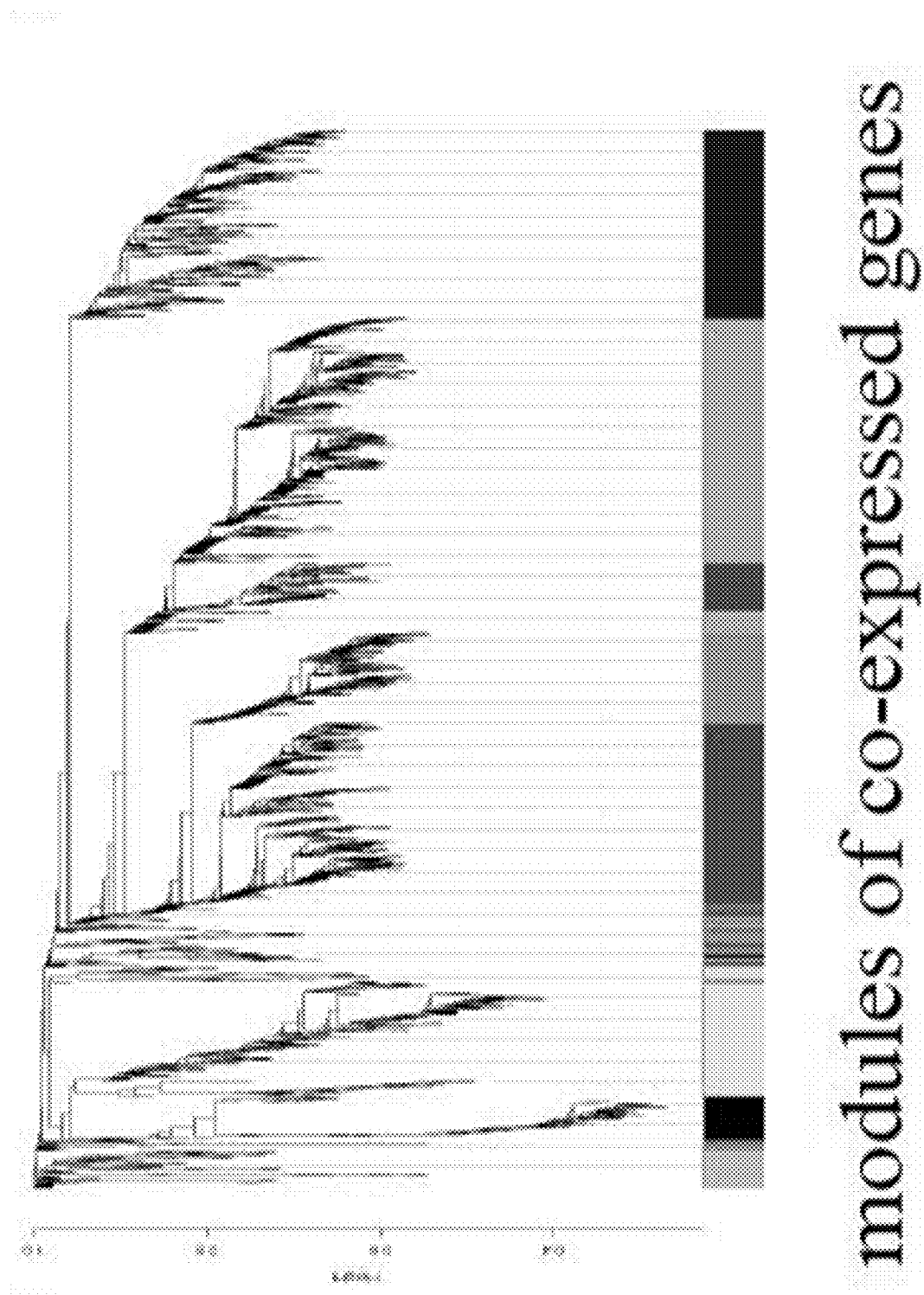
Figure 6C:
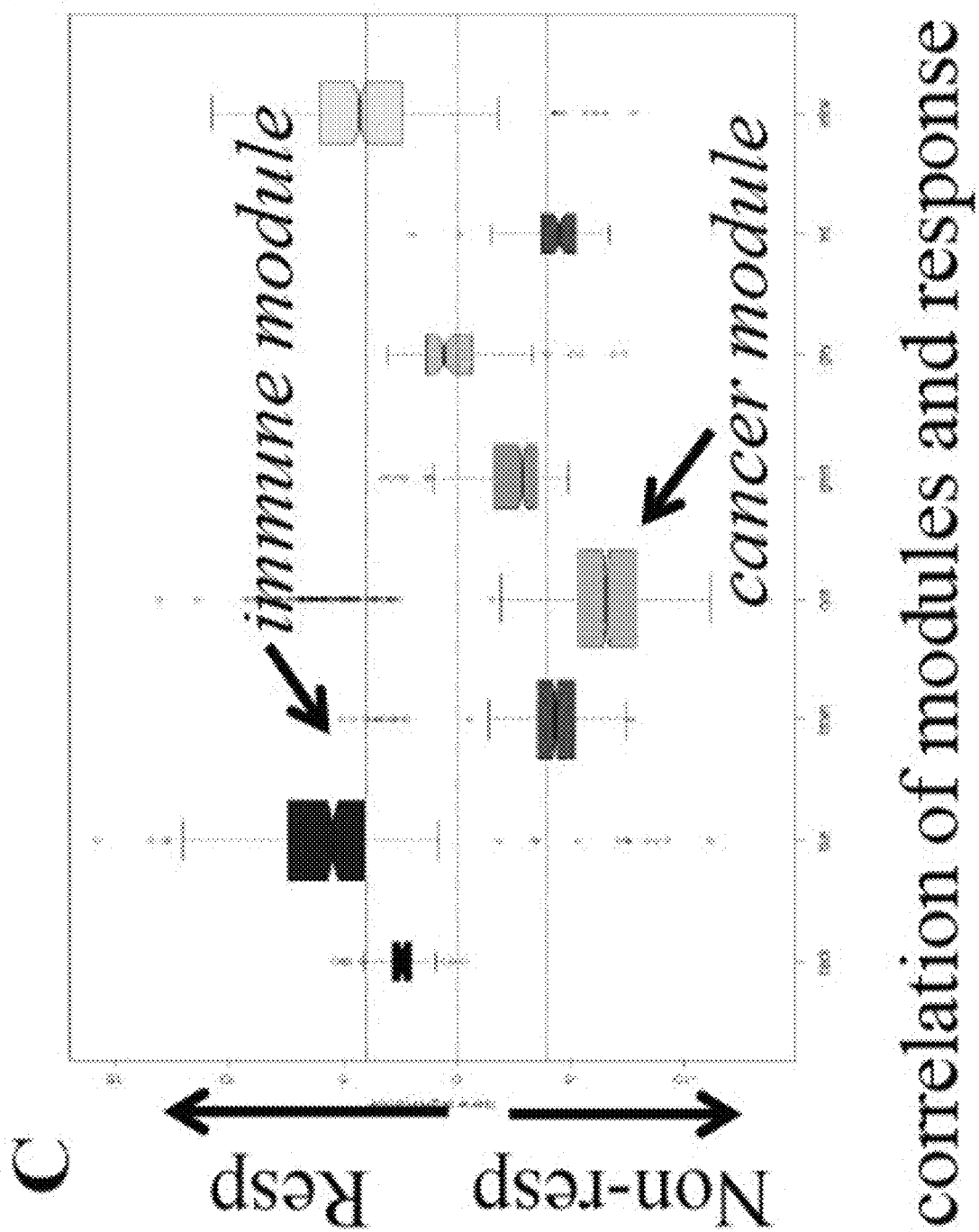
Figure 6D:
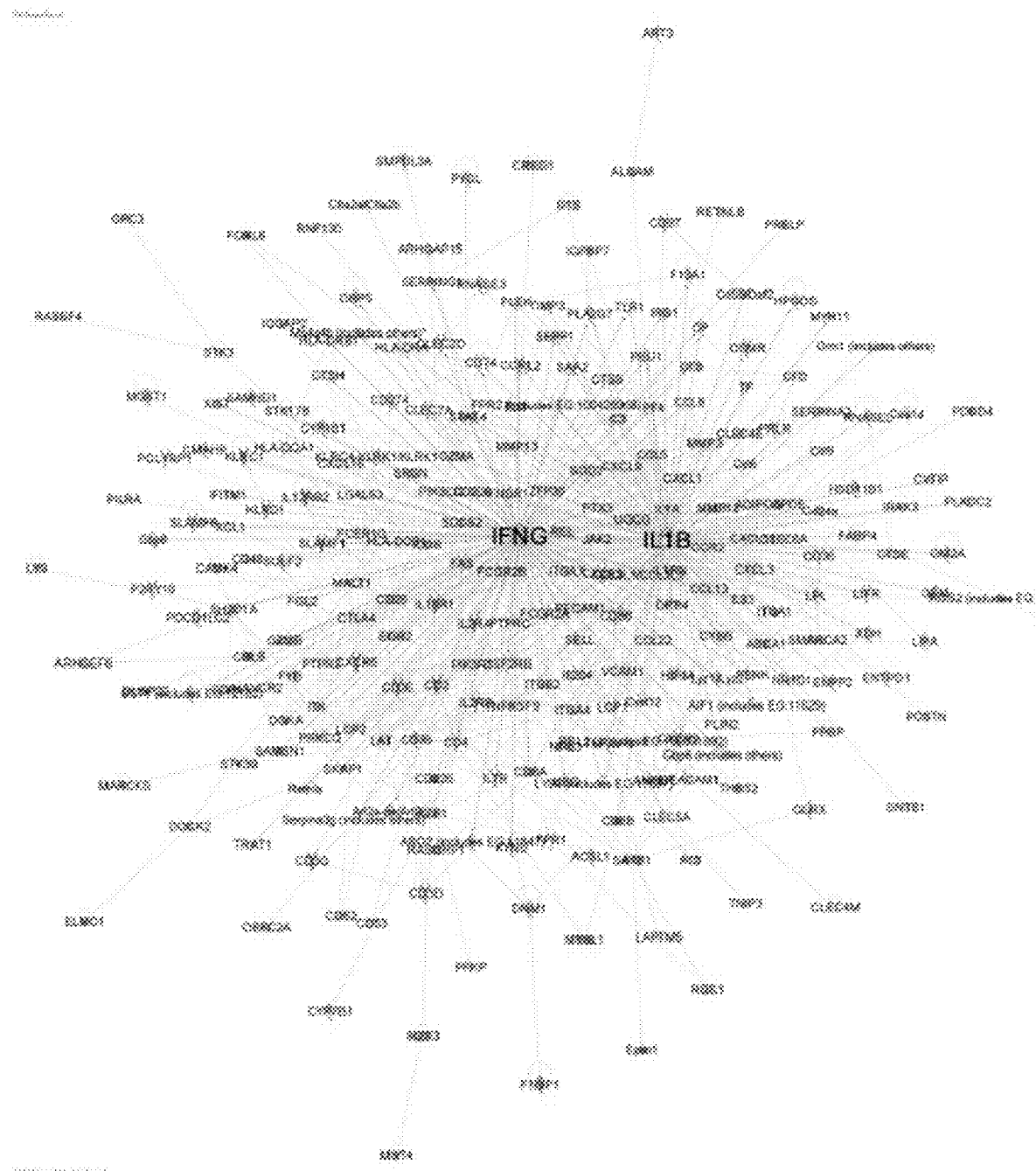
Figure 6E:
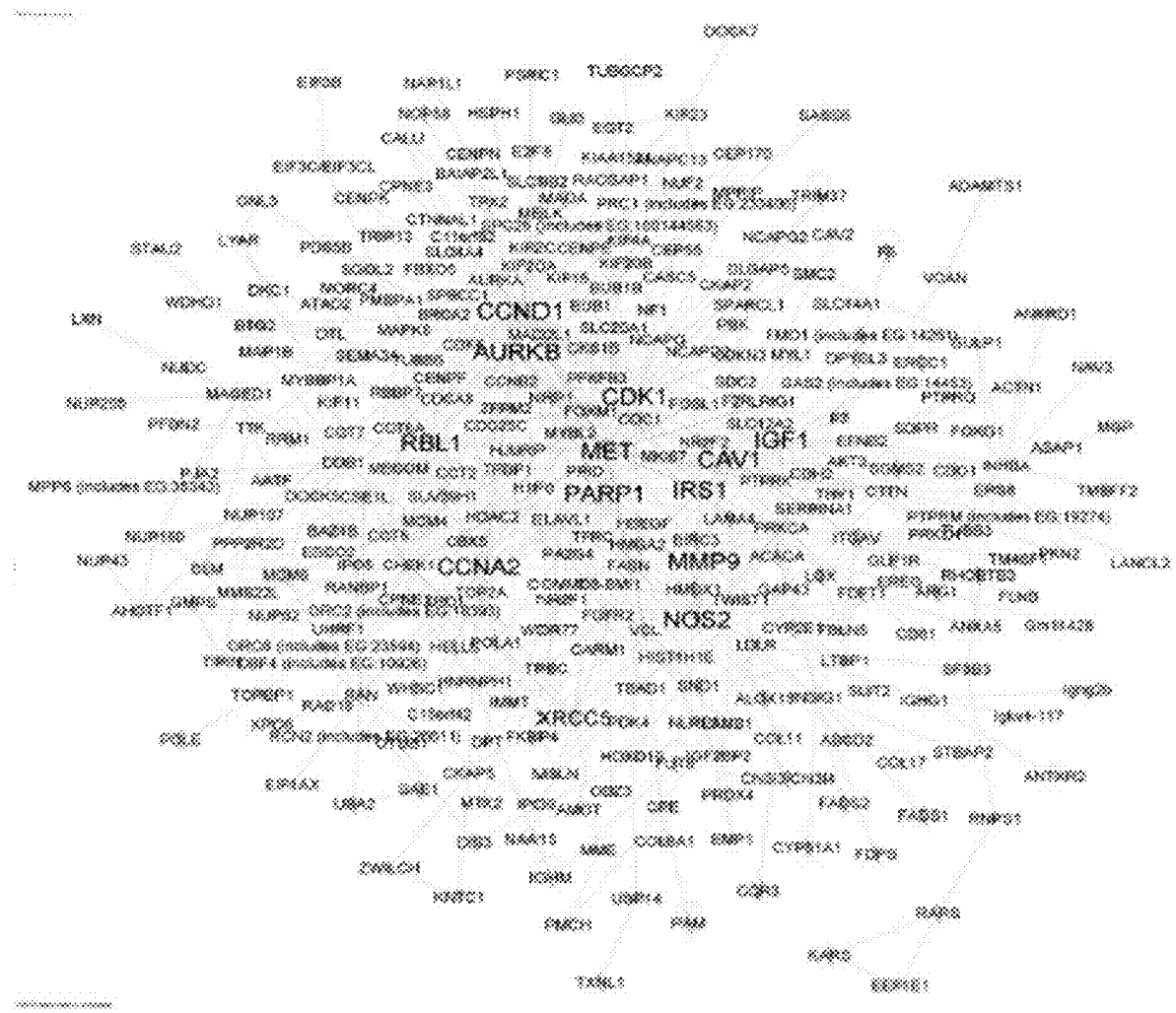

Network Analysis Pinpoints the Key Molecular Events in Immunotherapy-Induced Regression Next a gene expression analysis of responding vs non-responding tumours in anti-CTLA-4 treated mice was performed. Unsupervised hierarchical cluster analysis of microarray data of 30 mice (10 non-responders, 10 responders, 10 untreated) clearly showed that the three respective groups could be discriminated based on their general gene expression profile. Genes that correlated with a Th1 response (including IFNγ, STAT4, IL-18, IL-12, CXCR6 and several granzymes; FIG. 5), but also other less anticipated genes, such as iNOS and NK-ligands, were highly enriched in responding mice, when compared to non-responders or untreated (FIG. 5). Thus, the dual tumour model allows a robust and detailed analysis of the early cellular and molecular events that occur in an anti-CTLA-4 responsive tumour, without destroying the outcome readout (the remaining tumour), in the most informative setting: where responses are discordant between identically treated animals.

Next the inventors applied WGCNA of the microarray data in order to reconstruct the network based on coexpression of gene pairs and then identified several separate modules. Striking changes were observed in the gene networks, most notably upregulation of the blue module (blue module; FIG. 6) and downregulation of the cyan module in responders (cyan module; FIG. 6), when compared to non-responders and untreated mice. The blue module was highly enriched for genes involved in inflammation, which were highly upregulated in responders ('immune module'). The wiring diagram of the modules was reconstructed by incorporating mechanistic data (prior knowledge) from the literature stored in Ingenuity Systems Knowledge Base. As expected, the top hub genes included many cytotoxic T cell-related genes, chemokine receptors and genes involved in T cell proliferation. Less anticipated was the striking enrichment (10 out of 50 top hubs) of NK cell-related genes and NK-ligands. In addition, several genes that were associated with immune cellular function but had not been linked to effector responses before were found, as well as genes with limited prior knowledge on their function but correlating with (mammary or prostate) tissue regression under physiological circumstances.

The cyan module, which was downregulated in responding mice, was strongly enriched for genes involved in cell cycle regulation, adhesion and proliferation, which are central biological processes associated with cancer, and accordingly this module was named 'cancer module'. The majority of these genes were downregulated in responders, with the exception of several hubs, which were highly upregulated in responders only, indicating a possible reciprocal relationship with the cancer-related genes in the cancer module (see below).

Determining the Kinetics of the Developing Regressing Network

To determine the kinetics of a regressing tumour, tumours are removed from one side, and responsiveness to treatment is determined by monitoring the contralateral tumours. This is performed at several time points as to get a detailed and comprehensive view of the effector immune response during all its phases. Analyses are conducted on three groups of AB1-HA-bearing BALB/C mice (untreated, responders and non-responders, n=10/group, as described above in the preliminary data section), on days 3-5-7-9 after anti-CTLA-4 (day 7 being the moment that the tumour starts to decrease in size). Every time point is examined independently.

The sample size is based on previous studies, in which the inventors showed that experiments require a sample size of 30 to identify disease-associated modules that could be replicated in an independent dataset. In contrast to the earlier methods, the inventors use RNAseq, because it has single base resolution, superior sensitivity and dynamic range, and can detect novel genes and transcripts.

The RNA-Seq data is processed in R software using the Rsubread-featureCounts-voom-LIMMA pipeline. WGCNA is subsequently used for network analysis and module identification as per our earlier studies and hubs are identified using the Ingenuity Systems Pathway analysis tool. These experiments reveal how the network of the tumour develops in time up and past the tipping point of regression.

Preliminary Data for Aim #2
Targeting Hubs within the Response-Associated Modules Changes the Response to Anti-CTLA-4

Figure 7:
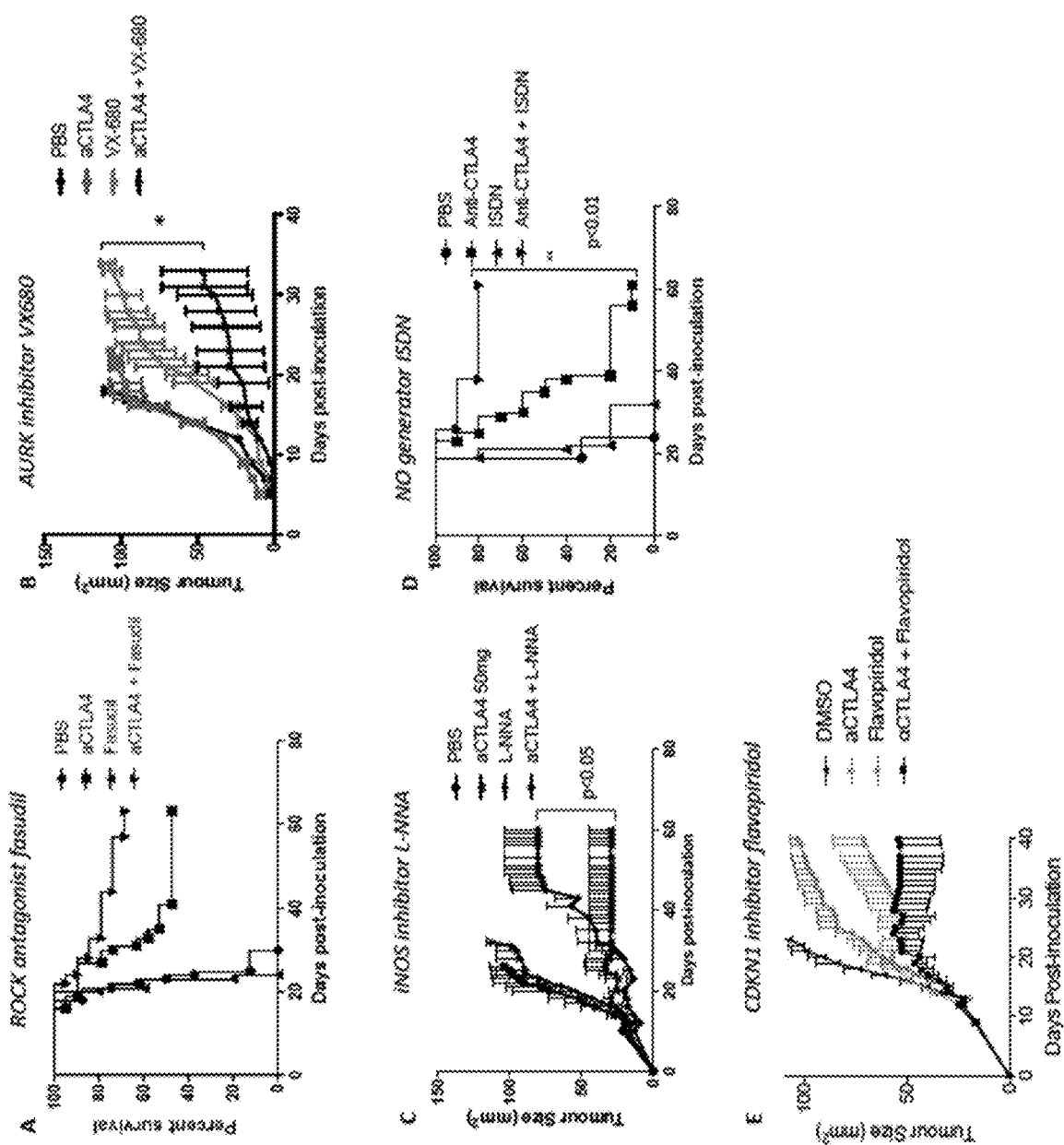
FIG. 7—Combining anti-CTLA-4 in combination with drugs that specifically target response-associated hubs changes treatment efficacy. AB1-HA mesothelioma-bearing mice were treated with anti-CTLA4 in combination with (A) the specific rho-kinase inhibitor fasudil or (B) Aurora Kinase inhibitor VX-680. (C) Inhibition of iNOS with the inhibitor L-NNA abrogated the anti-tumour effect, while (D) amplification of the iNOS pathway through co-treatment with ISDN increased the response rate to anti-CTLA-4, as predicted by the network analysis and (E) so did co-treatment with the CDKN1 inhibitor flavopiridol.
Figure 9:
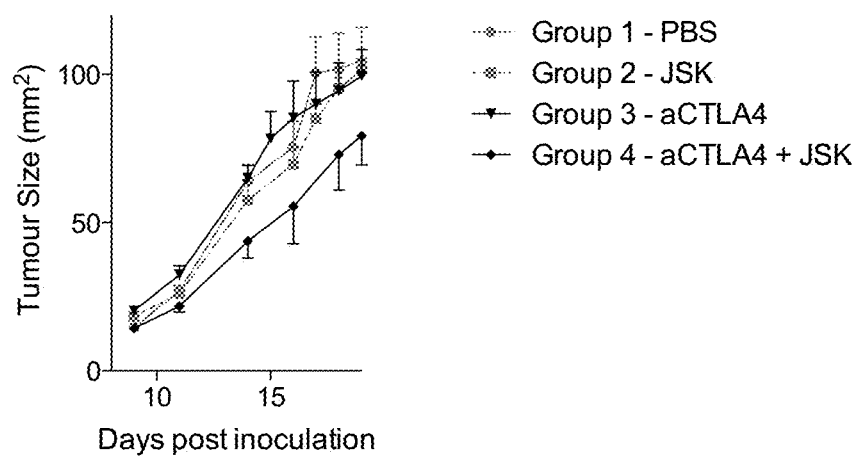
FIG. 9—Combining anti-CTLA4 with NO generator JS-K, which is from a different class of drugs than ISDN, also improves the clinical benefit of anti-CTLA4 in AB1-HA tumour bearing mice.

As noted above following the above methods the inventors identified several hub genes in the cancer module that were involved in Rho kinase activation, and were downregulated in responders only. For this reason, the inventors treated mice with anti-CTLA-4 in combination with fasudil, a Rho kinase-specific inhibitor that is used in patients with cerebral vasospasm. Fasudil alone did not result in any growth delay, but in combination with anti-CTLA-4 it increased the response rate (FIG. 7a). These data suggest that by pharmaceutically targeting several hubs within the cancer module the inventors could indeed enhance the response rate to anti-CTLA-4. The inventors also identified Aurora Kinase as one of the top hubs in the cancer module, which was downregulated in responders. They therefore tested specific Aurora Kinase inhibitor VX-680 in combination with anti-CTLA-4. VX-680 is currently in clinical development for several malignancies in which immune checkpoint blockade has not been successful such as breast, colon and pancreas cancer. Indeed they found that the anti-cancer effect of anti-CTLA-4 was significantly increased by co-treatment with VX-680 (FIG. 7b). The robustness of this approach is exemplified by a third example. The inventors found that inducible nitric oxide synthase (iNOS) was a hub in the cancer module, but was highly upregulated in responding mice, indicating a reciprocal relationship. To validate iNOS as an important mediator of the response, the inventors specifically inhibited iNOS using L-NNA and observed that indeed the efficacy of anti-CTLA-4 was diminished (FIG. 7c). Conversely, when the inventors amplified iNOS by co-treating the mice with NO-donor isosorbidedinitrate (ISDN), they were able to increase the therapeutic efficacy (FIG. 7d), suggesting that indeed this upregulated gene was a key controller of the cancer module. In addition, when JS-K was used as nitric oxide generator (which unlike the nitrate ISDN is a GST-activated nitric oxide generator), similar results were found (FIG. 9). These data confirm the power and feasibility of using network analysis to identify cooperative targets for drug development.

Identification of Pleiotropic Drugs that Affect the Network

By using computational analyses to compare the microarray data with data from publically available 'drug repositioning' databases containing genome-wide gene expression data from drug-treated cell lines, the inventors identified several potential candidate compounds that could increase expression levels of genes in the immune module and/or decrease expression levels of genes in the cancer module and thus mimic the network of responding cancer. The identified drugs that were statistically significant below a specified threshold (p-value <0.01) are listed in Table 5. The table contains the name of each drug (Drug name) and the cell line that the data was derived from (Cell Line). The other columns provide additional information. The "mean connectivity" measures the average strength of the pattern match between the immune/cancer module genes in the responding cancer and in the cell lines. The "n" refers to the number of independent experiments that were conducted for the given drug in a given cell line. The "enrichment" measures the enrichment of the n experiments amongst a ranked list of all experiments. The "p-value" is the probability that the enrichment was observed by chance. The "specificity" provides a measure of the uniqueness of the pattern match between the responding cancer and the drug responses based on a large number of past results generated using a collection of diverse signatures.

TABLE 5

Candidate drugs that can modulate expression levels of genes in the immune/cancer modules in a manner (increased or decreased) that is consistent with the network of responding cancer.

| Drug name | Cell line | Mean connectivity | n | enrichment | p-value | specificity |
|---|---|---|---|---|---|---|
| trichostatin A | PC3 | 0.654 | 55 | 0.529 | 0 | 0.44 |
| trichostatin A | MCF7 | 0.523 | 92 | 0.382 | 0 | 0.7156 |
| resveratrol | MCF7 | 0.811 | 6 | 0.805 | 0.00008 | 0.0895 |
| tretinoin | MCF7 | 0.602 | 13 | 0.578 | 0.00008 | 0.0659 |
| LY-294002 | MCF7 | 0.487 | 34 | 0.367 | 0.0002 | 0.3421 |
| vorinostat | MCF7 | 0.669 | 7 | 0.738 | 0.00022 | 0.3158 |
| harmine | MCF7 | 0.945 | 2 | 0.988 | 0.00026 | 0.0066 |
| sirolimus | MCF7 | 0.396 | 25 | 0.401 | 0.0004 | 0.2711 |
| pyridoxine | MCF7 | 0.882 | 2 | 0.985 | 0.00044 | 0.0073 |
| phenoxybenzamine | MCF7 | 0.808 | 3 | 0.929 | 0.00064 | 0.1921 |
| alpha-estradiol | MCF7 | 0.67 | 9 | 0.624 | 0.00064 | 0.042 |
| protoveratrine A | MCF7 | 0.868 | 2 | 0.975 | 0.00099 | 0 |
| trifluoperazine | MCF7 | 0.491 | 9 | 0.599 | 0.00116 | 0.1971 |

TABLE 5-continued

Candidate drugs that can modulate expression levels of genes in the immune/cancer modules in a manner (increased or decreased) that is consistent with the network of responding cancer.

| Drug name | Cell line | Mean connectivity | n | enrichment | p-value | specificity |
|---|---|---|---|---|---|---|
| astemizole | PC3 | 0.869 | 2 | 0.972 | 0.00123 | 0.0337 |
| galantamine | MCF7 | 0.911 | 2 | 0.972 | 0.00125 | 0.0168 |
| alexidine | PC3 | 0.857 | 2 | 0.967 | 0.00185 | 0.033 |
| 175029-0000 | PC3 | 0.705 | 4 | 0.81 | 0.00247 | 0.0764 |
| prochlorperazine | MCF7 | 0.661 | 9 | 0.572 | 0.00252 | 0.1841 |
| tomatidine | MCF7 | 0.89 | 2 | 0.962 | 0.00256 | 0.0164 |
| meticrane | PC3 | 0.855 | 2 | 0.958 | 0.00308 | 0.0303 |
| thioridazine | PC3 | 0.719 | 5 | 0.718 | 0.00409 | 0.1636 |
| chlorpromazine | MCF7 | 0.564 | 11 | 0.5 | 0.00418 | 0.0196 |
| sulconazole | MCF7 | 0.851 | 2 | 0.95 | 0.00449 | 0.051 |
| seneciphylline | MCF7 | 0.854 | 2 | 0.946 | 0.00535 | 0.0945 |
| hydrocotarnine | MCF7 | 0.833 | 2 | 0.946 | 0.00557 | 0.0141 |
| DL-thiorphan | MCF7 | 0.857 | 2 | 0.942 | 0.00638 | 0.0147 |
| thioguanosine | MCF7 | 0.824 | 2 | 0.941 | 0.0066 | 0.1167 |
| dacarbazine | MCF7 | 0.858 | 2 | 0.94 | 0.0069 | 0.0348 |
| chrysin | MCF7 | 0.865 | 2 | 0.937 | 0.00763 | 0.0234 |
| cloperastine | PC3 | 0.808 | 2 | 0.935 | 0.00799 | 0.0225 |
| pancuronium bromide | MCF7 | 0.831 | 2 | 0.935 | 0.00809 | 0.0315 |
| carbarsone | MCF7 | 0.872 | 2 | 0.934 | 0.00827 | 0.0161 |
| corynanthine | MCF7 | 0.801 | 2 | 0.928 | 0.00984 | 0 |
| Prestwick-674 | MCF7 | 0.751 | 3 | 0.83 | 0.00988 | 0.0486 |

Figure 8:
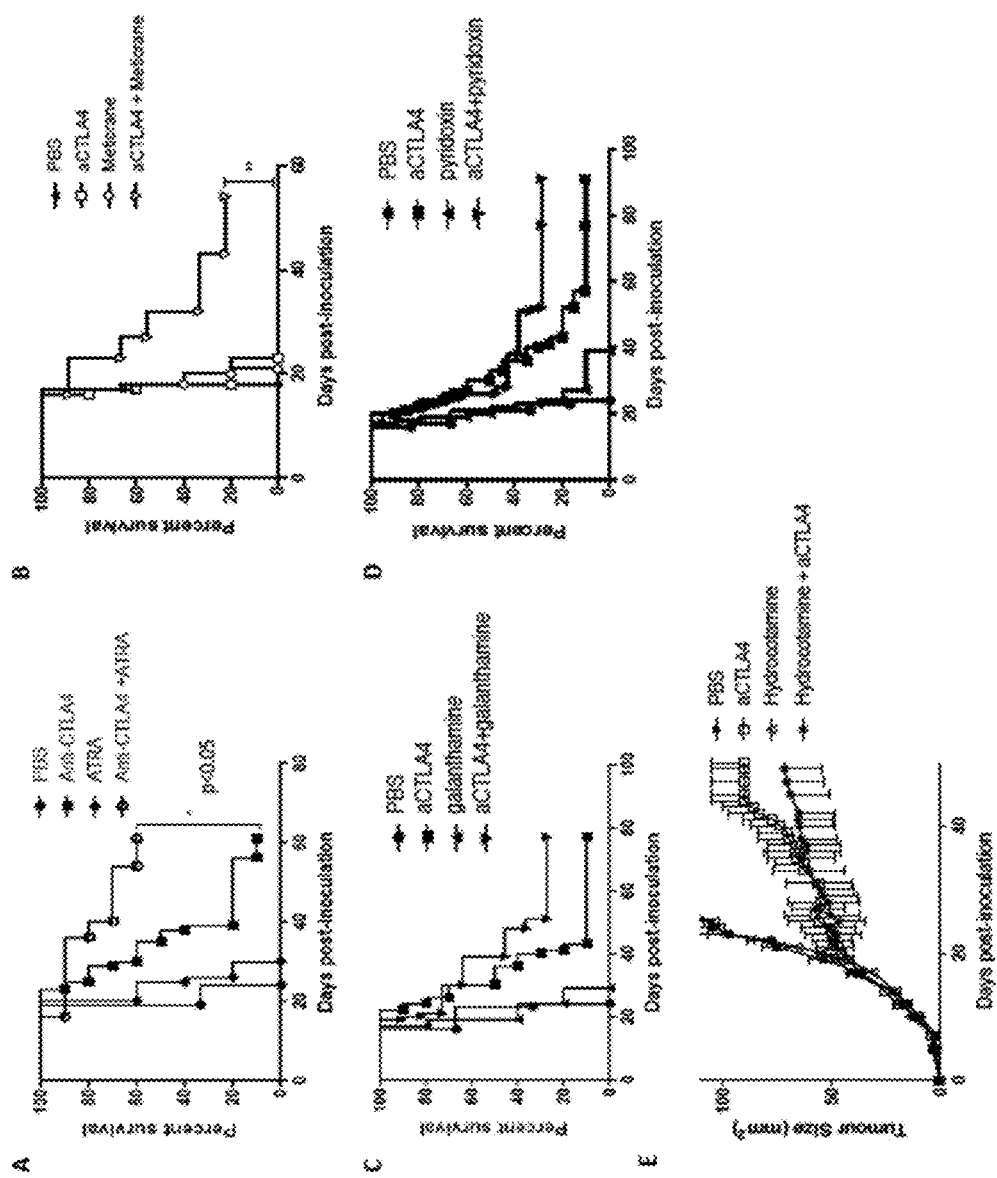
FIG. 8—Drugs that phenocopy the response-associated modules increase the response rates to immune checkpoint blockade. We co-treated AB1-HA bearing mice with anti-CTLA-4 in combination with response network-targeted drugs (A) ATRA, (B) meticrane, (C) galantamine and (D) pyridoxine and (E) hydrocotamine and indeed found an increased anti-tumour response for all these drugs.

Using this approach the inventors successfully identified multiple candidate drugs that were indeed able to enhance the response rate to checkpoint blockade, as shown in FIG. 8, demonstrating the power and validity of the approach. These included compounds that were developed for a variety of disorders, such as psychiatric and dermatological diseases. As a proof of concept, the inventors tested four compounds: All-trans Retinoic Acid (ATRA, used in acneform skin disease and as a stem cell differentiation inducer in leukemia), meticrane (a diuretic used in Japan for the treatment of hypertension) galanthamine (used in the treatment of Alzheimer's disease) and pyridoxine (vitamin B6, used to prevent side-effects from anti-tuberculosis drugs). The inventors co-treated AB1-HA-bearing mice with anti-CTLA-4 in combination with these drugs and indeed found a clear effect when they combined these treatments (FIG. 8). Importantly, the majority of these drugs have never been associated with any anti-tumour or pro-immune effect. These data demonstrate the power of using repositioned drugs to mimic the network of checkpoint blockade-responsive tumours, in order to increase the response rate to this treatment.

Figure 10:
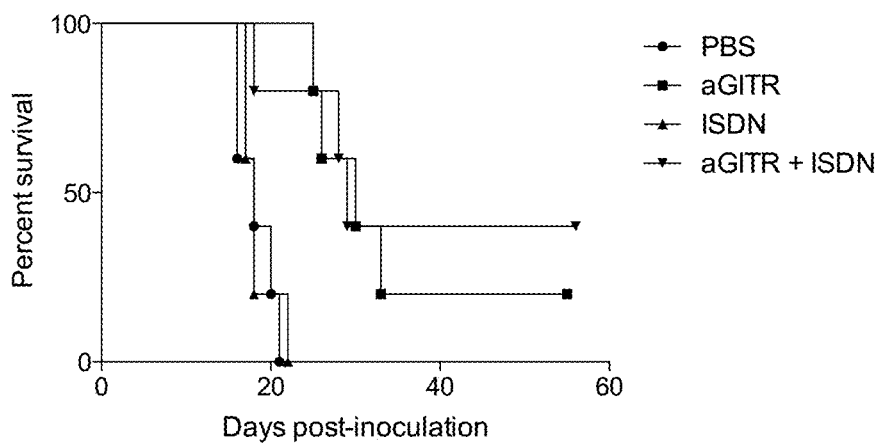
FIG. 10—Drugs that were predicted to work in synergy to anti-CTLA4 blockade, also synergize with other immune checkpoint blocking antibodies. We cotreated AB1-HA tumour bearing mice with anti-GITR in combination with ISDN and observed an improved survival for the combination.
Figure 11A:
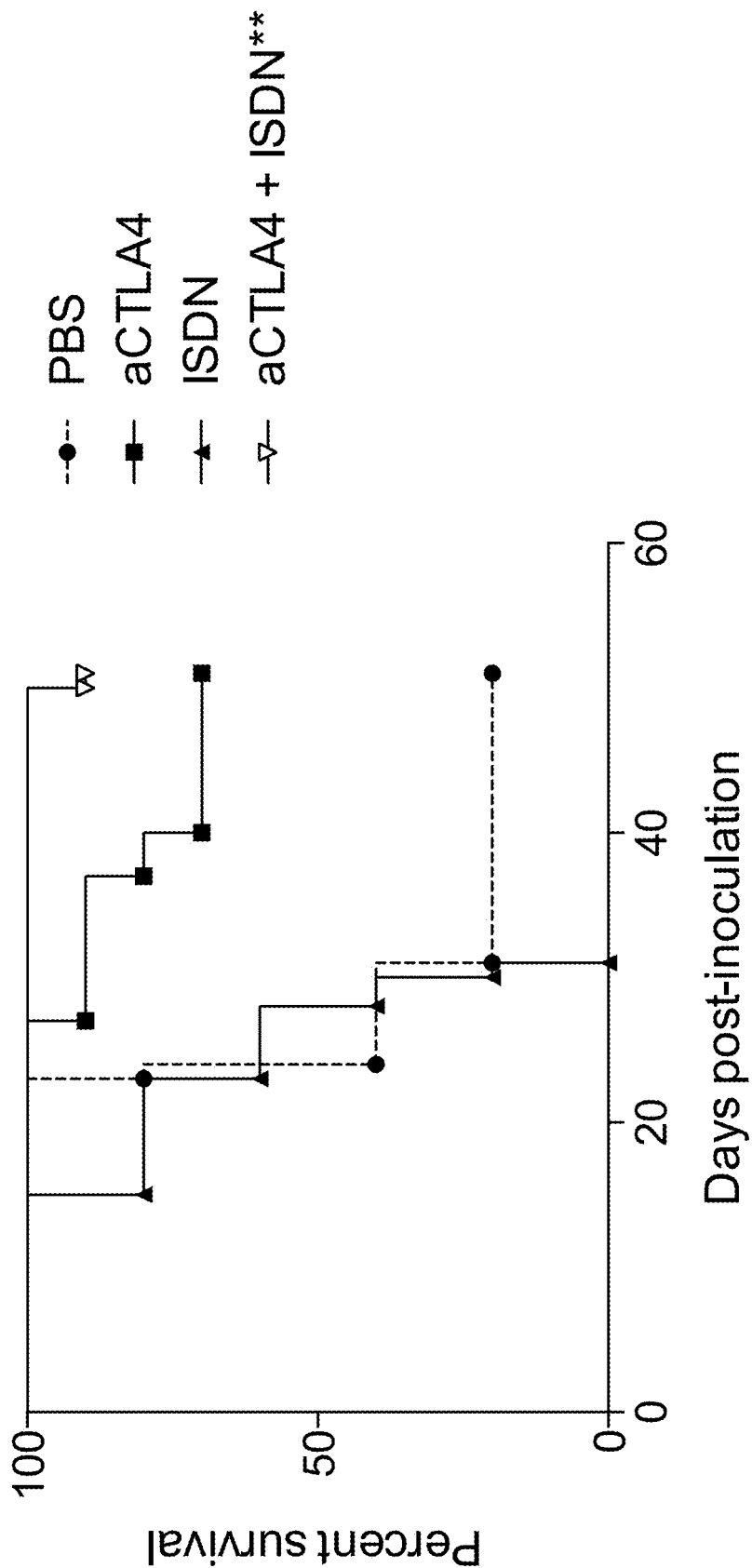
FIG. 11—Drugs that were predicted to work in synergy with checkpoint blockade in the AB1-HA mesothelioma model also synergize in other unrelated cancers. Mice were inoculated with Renca kidney cancer cells and were treated with anti-CTLA4 in combination with (A) ISDN or (B) ATRA. For both drugs an improved survival was observed for the combination therapy in this second tumour model. (C) The combination therapy with anti-CTLA4 and ISDN also induced a complete regression in a substantial proportion of mice in lung cancer model Line-1, while this was not observed for either treatment alone.
Figure 11B:
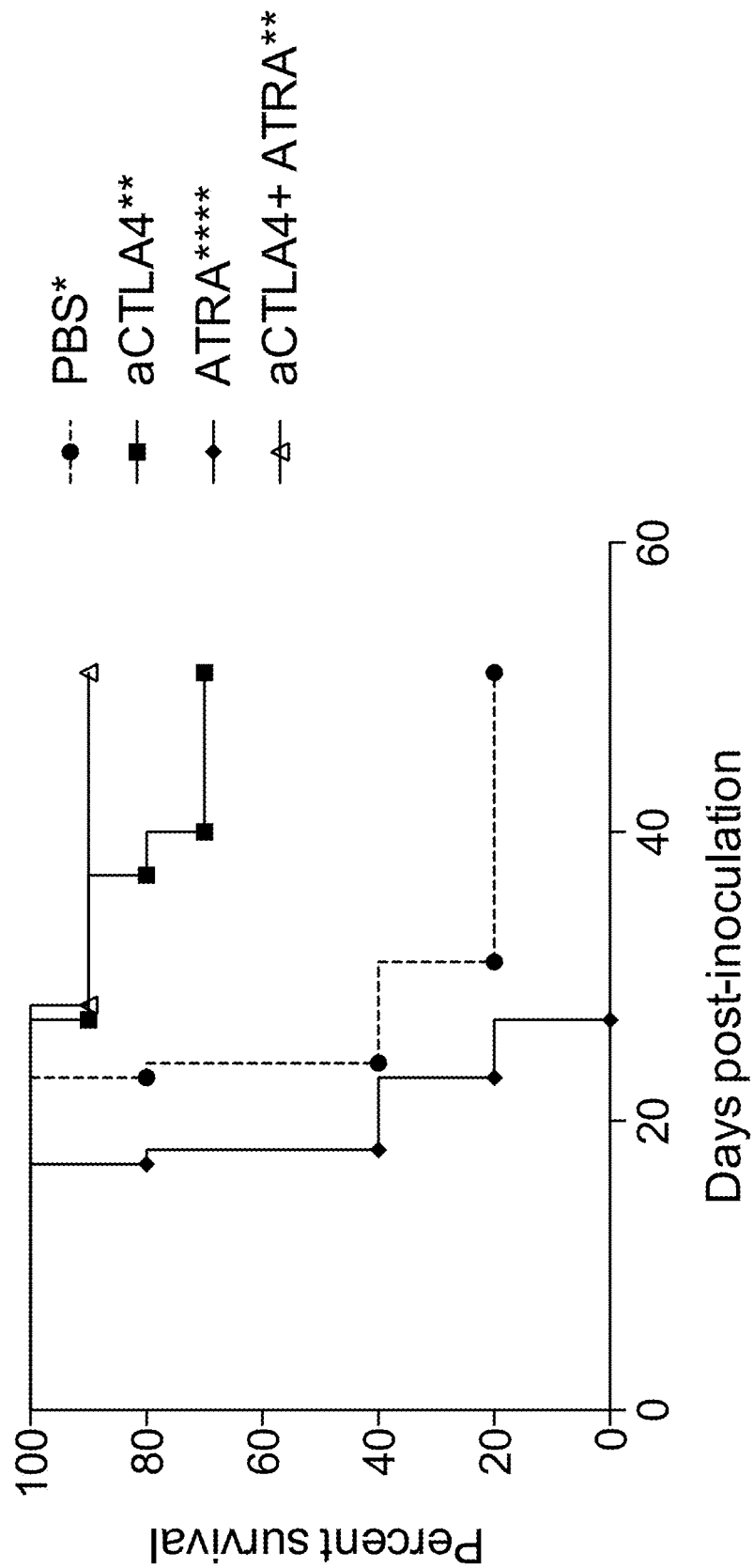
Figure 11C:
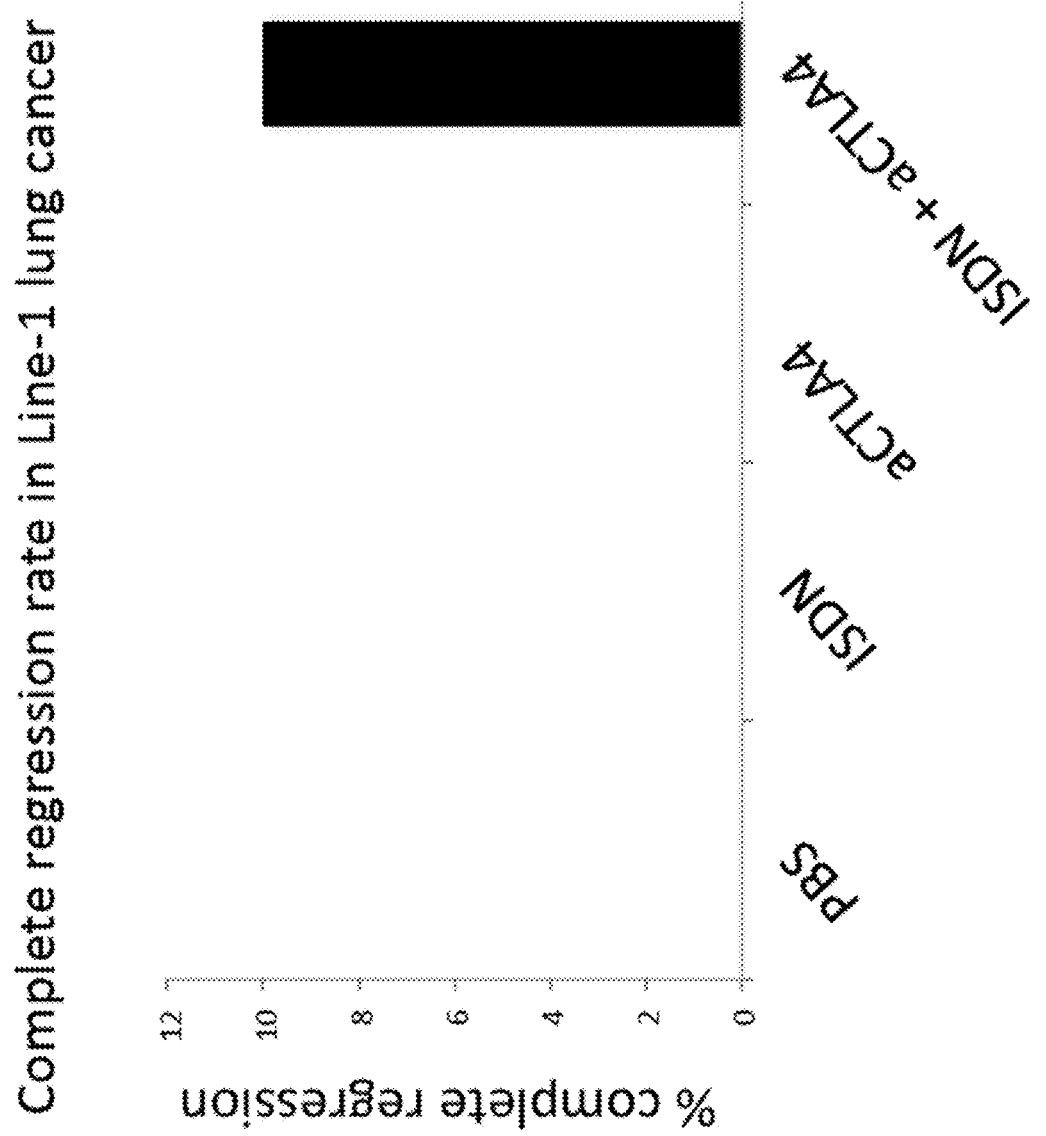

The inventors also tested whether the findings could be extended to other checkpoint-blocking antibodies, different from anti-CTLA4, and found that indeed the efficacy of checkpoint blockade with anti-GITR could equally be improved by co-treatment with ISDN (FIG. 10). In addition, they verified whether the findings could be replicated in another cancer model, different from mesothelioma, and found that ISDN and ATRA could indeed improve the clinical efficacy of CTLA4 blockade in Renca kidney cancer and in Line-1 lung cancer, demonstrating that the findings can be extrapolated to multiple cancer types (FIG. 11).

Methods and Materials

Mice

BALB/c (H-2d) mice were obtained from the Animal Resources Centre (Canning Vale, Australia) and were maintained under standard conditions (M-Block Animal Facility, Queen Elizabeth II Medical Centre, The University of Western Australia). All mice used in these studies were between 8-12 weeks of age. All animal experiments were conducted according to The University of Western Australia Animal Ethics Committee approvals (protocol RA/3/100/1139) and the code of conduct of the National Health and Medical Research Council of Australia. The Western Australia Animal Ethics Committee specifically approved this study.

Cell Lines

The MHC class I-positive, class II-negative, highly tumorigenic and poorly immunogenic BALB/c-derived asbestos-induced mouse mesothelioma cell line AB1, transfected with the influenza HA gene (AB1-HA) has been described before (Marzo, A. L. et al. Tumor antigens are constitutively presented in the draining lymph nodes. Journal of immunology 162, 5838-5845 (1999); Nowak, A. K. et al. Induction of tumor cell apoptosis in vivo increases tumor antigen cross-presentation, cross-priming rather than cross-tolerizing host tumor-specific CD8 T cells. Journal of immunology 170, 4905-4913 (2003); Lesterhuis, W. J. et al. Synergistic effect of CTLA-4 blockade and cancer chemotherapy in the induction of anti-tumor immunity. PloS one 8, e61895, doi:10.1371/journal.pone.0061895 (2013)). The poorly immunogenic and highly tumorigenic Renca cell line, originally derived from a spontaneous renal cortical adenocarcinoma (Murphy, G. P. & Hrushesky, W. J. A murine renal cell carcinoma. Journal of the National Cancer Institute 50, 1013-1025 (1973)), was obtained from ATCC where the identity of the cell line was validated. Cell lines were maintained in RPMI 1640 (Invitrogen, Mulgrave, Australia) supplemented with 20 mM HEPES, 0.05 mM 2-mercaptoethanol, 100 units/mL penicillin (CSL, Melbourne, Australia), 50 µg/mL gentamicin (David Bull Labs, Kewdale, Australia), and 10% FCS (Invitrogen). AB1-HA cells were maintained in media containing the neomycin analogue geneticin (Invitrogen) at a final concentration of 400 µg/mL. All cell lines were regularly tested and remained negative for Mycoplasma spp.

Antibodies

The anti-CTLA-4 (clone 9H10) and anti-GITR monoclonal antibody were prepared and purified at the Monoclonal Antibody Facility, WAIMR (Perth, Australia). The CTLA-4 hybridoma was a kind gift from Prof. J. P. Allison (Memorial Sloan Kettering Cancer Centre, New York, US). The anti-PD-L1 and anti-PD-1 monoclonal antibodies were prepared and purified by Bioceros BV.

Tumor Challenge and Anti-CTLA-4 Treatment Protocols Including Surgery

Initial Experiments into Symmetry of Response:

BALB/c mice were inoculated subcutaneously (s.c.) with $5 \times 10^5$ AB1-HA cells on both flanks on day 0. They were treated with anti-CTLA-4 on day 5 or 6 intraperitoneally (i.p.). In these experiments we aimed for a response rate of approximately 40-60%, but depending on the batch of the anti-CTLA-4 antibody we observed slight differences in response rates. We therefore optimized dosing for each subsequent batch, using either single dose of 100 or 200 μg per mouse. Non-responders and responders were matched for dose.

In only 11% of the mice the response was asymmetric: regrowth appeared in a previously responding one-sided lesion, which always occurred within 40 days. Sham surgery did not affect the symmetry of response (data not shown). Therefore, we can remove one tumour, leaving the other in situ and subsequently infer the fate of the material we have removed and analysed by monitoring the growth of the remaining indicator tumour for at least 40 days. This gives us a window on the key controlling events in otherwise identical tumours before regression is manifest.

Subsequent Experiments with One-Sided Tumor Removal:

After having confirmed that sham surgery did not affect the symmetry of response (data not shown), we subsequently initiated experiments in which on the day of response initiation (the 'tipping point', 7 days after anti-CTLA-4 administration) we removed one of the two tumors. Tumors from 4 different experiments were used, in which the mice were treated on day 5 or 6 with anti-CTLA-4 200 μg i.p. and the tumor was removed 7 days later. Mice were anesthetized with isoflurane for not more than 5 minutes, during which the s.c. tumor was removed through an incision in the flank and instantly fully submerged in RNAlater (Life Technologies, Australia), after which the surgical wounds were sutured using 5/0 vicryl continuous sutures (Ethicon, North Ryde, Australia). Mice were placed under a heat lamp for recovery.

The following weeks the remaining indicator tumor was measured using digital micro-calipers at least three times per week and based on its growth characteristics the mice were divided into three different groups:

1—Responders: Tumor was evident as a palpable subcutaneous nodule of at least 5 mm² on the day of surgery of the other tumor (which also should be palpable) and it regressed to 0 mm² and stayed undetectable for more than 40 days post-inoculation.

2—Non-responders: Tumor was evident as a palpable subcutaneous nodule of at least 5 mm² on the day of surgery of the other tumor (which also should be palpable) and it continued to progress, i.e. there was no sign of slowing of growth or a partial decrease. When the tumor size reached 100 mm2 mice were euthanized following regional animal ethics guidelines.

3—Intermediate responders: Not a clear responder or non-responder, i.e. there was either a full regression but followed by tumor growth within the observed time period (of at least 40 days), partial regression, delayed or slowed outgrowth or a tumor of <5 mm² at time of surgery. These mice were excluded from analysis.

As a control group, tumors were removed on day 13 from mice that had been treated with 100 μl PBS on day 6 after tumor inoculation.

We performed gene expression microarray analysis comparing anti-CTLA-4-treated mice that had shown full regression of the contralateral tumor without reoccurrence in the following 2 months (responders, n=10) with mice that had continuous growth of the contralateral tumors (non-responders, n=10). We used PBS-treated mice as control (n=10); mice with an intermediate response were discarded.

RNA Isolation

The tumors were stabilized in RNAlater (Life Technologies, Australia) and stored at −80° C. The tumors were disrupted in TRIzol (Life Technologies, Australia) employing a TissueRuptor rotor-stator homogenizer (QIAgen, Australia). After addition of chloroform and aqueous phase separation, the samples were purified on RNeasy MinElute columns (QIAgen, Australia). The integrity of the RNA samples was confirmed on the Bioanalzyer (Agilent Technologies, USA).

Microarrays

Total RNA samples of the 3 groups of 10 tumors/mice each were labeled and hybridized to Mouse Gene 1.0 ST microarrays (Affymetrix, USA) at the Ramaciotti Centre for Gene Function Analysis (University of New South Wales, Australia). The microarray data was high quality; mean raw intensity of pm probes (±sd)=398.15±89.8; discrimination of positive versus negative control probes=0.855±0.024; median absolute deviation of the residuals mean=0.334±0.05; relative log expression mean=0.228±0.07.

Network Analysis

The microarray data was preprocessed in R employing the Factor Analysis for Robust Microarray Summarization (qFARMS) algorithm (Hochreiter S et al. Bioinformatics. 2006 Apr. 15; 22(8): 943-9. Pubmed ID: 16473874). A custom chip description file (mogene10stmmentrezg, versions 16-18) was used to map probe sets to genes based on current genome annotations (Dai M et al Nucleic Acids Res. 2005 Nov. 10; 33(20): e175. Pubmed ID: 16284200). The informative/non-informative calls algorithm was employed to filter out noisy probe sets (Talloen W et al Bioinformatics. 2007 Nov. 1; 23(21): 2897-902. Pubmed ID: 17921172). A coexpression network was constructed employing the weighted gene coexpression network analysis algorithm (WGCNA) (Zhang B and Horvath S. Stat Appl Genet Mol Biol. 2005; 4: Article17. Pubmed ID: 16646834, Bosco et al J Immunol. 2009 May 15; 182(10): 6011-21. Pubmed ID: 19414752). Genes/modules associated with response to treatment were identified using moderated t-statistics, with False Discovery Rate control for multiple testing (Smyth GK. Stat Appl Genet Mol Biol. 2004; 3: Article3. Pubmed ID: 16646809). The wiring diagram of the modules was reconstructed using the Ingenuity Systems KnowledgeBase of expert curated functional data from published studies (Ingenuity Systems Knowledgebase; Bosco et al J Allergy Clin Immunol. 2012 January; 129(1): 88-94. Pubmed ID: 22112518). Hubs were prioritized for drug targeting studies by plotting the gene expression data along axes of differential expression and intramodular coexpression network connectivity (Zhang B and Horvath S. Stat Appl Genet Mol Biol. 2005; 4:Article17. Pubmed ID: 16646834, Bosco et al J Immunol. 2009 May 15; 182(10):6011-21. Pubmed ID: 19414752).

Computational Drug Repositioning

This analysis was based on the connectivity map (cMap) database, which comprises gene expression profiles from a panel of human cell lines induced by 1,309 drug compounds (Lamb J et al Science. 2006 Sep. 29; 313(5795):1929-35. Pubmed ID: 17008526). Modules associated with response to treatment were identified as described above. Human orthologs of the mouse genes within these response modules were identified using a conversion table from the Mouse Genome Informatics database (http://www.informatics.jax.org/). Human orthologs were then mapped to Affymetrix hgu133a probe sets using annotation packages from Bioconductor (http://www.bioconductor.org/). Up and down regulated probe sets were defined by contrasting gene expression levels in tumors from responder versus nonresponder mice. The probe sets were queried against the cMap database using software from the Broad Institute (https://www.broadinstitute.org/cmap/).

Drugs and Treatment Schedules for In Vivo Treatment

For in vivo intervention studies using network-targeted agents BALB/c mice were inoculated with $5\times10^5$ AB1-HA mesothelioma cells, or Line-1 lung cancer cells, or Renca kidney cancer cells, as indicated, s.c. on one flank. Anti-CTLA-4 was administered i.p. on day 10 at a single dose of 100 µg per mouse. The following drugs were administered in combination with anti-CTLA-4. All drugs were started with dosing on day 10, together with the anti-CTLA-4 unless otherwise indicated. The dosages were based on published studies, unless otherwise stated.

L-NNA (Cayman Chemicals, Mic, USA) was dissolved in PBS to a concentration of 1 mg/mL and sonicated to dissolve. Mice received i.p. injections of 15 mg/kg bodyweight every second day for 10 doses i.p, post αCTLA4 treatment. This dose regime was based on literature (Piotrovskij, V. et al. Dose-ranging study of NG-nitro-L-arginine pharmacokinetics in rats after bolus intravenous administration. *Xenobiotica; the fate of foreign compounds in biological systems* 24, 663-669, doi:10.3109/00498259409043268 (1994)), combined with our own dose-optimizing study in which we sequentially treated 2 groups (n=3/group) of standard BALB/c mice with 15 mg/kg or 30 mg/kg for 10 days and monitored weight and clinical scores. We observed weight loss of around 15% with the highest dose. Therefore, we decided to use the lower dose.

Isosorbide dinitrate (Toronto Research Chemicals Inc, To, Canada) was dissolved to 4 mg/mL in DMSO. Mice received daily i.p. injection for 14 days at 200 µg/mouse post αCTLA4 treatment (Pipili-Synetos, E. et al. Inhibition of angiogenesis, tumour growth and metastasis by the NO-releasing vasodilators, isosorbide mononitrate and dinitrate. *British journal of pharmacology* 116, 1829-1834 (1995)).

All-trans-retinoid acid (Selleck Chemicals, Tx, USA) was dissolved in DMSO to a concentration of 100 mg/ml in DMSO and diluted to a final concentration of 10 mg/ml in PBS. Mice received daily i.p. injections at a dose of 10 mg/kg bodyweight for 10 days post αCTLA4 treatment.

VX-680 (AdooQ Bioscience, CA, USA) was dissolved in DMSO to a concentration of 32 mg/mL. Mice received daily i.p. injections at a dose of 80 mg/kg bodyweight for 14 days post αCTLA4 treatment (Li, Y. et al. VX680/MK-0457, a potent and selective Aurora kinase inhibitor, targets both tumor and endothelial cells in clear cell renal cell carcinoma. *American journal of translational research* 2, 296-308 (2010)).

Meticrane (Sigma, MO, USA) was dissolved in DMSO to a concentration of 160 mg/mL. Mice received daily i.p. injections at a dose of 400 mg/kg bodyweight for 10 days post αCTLA4 treatment. This dose was based on our own dose-optimizing studies, since we could not find dosing studies in mice in the literature. The diuretic meticrane is approved as an antihypertensive in Japan and is used at doses of 150-300 mg once daily; the reported LD50 for mice after i.p. administration is 10 g/kg (http://chem.sis.nlm.nih.gov/chemidplus/rn/1084-65-7; Lawton, W. J. & Chatterjee, K. in Cardiac Drugs (eds K. Chatterjee & E. J. Topol) 72-157 (Jaypee Brothers Medical Publishers Ltd., 2013)). We treated 3 groups of standard BALB/c mice consecutively (n=3/group) with increasing doses of meticrane i.p. (100 mg/kg; 200 mg/kg and 400 mg/kg) for 10 days and monitored weight and clinical scores (Workman, P. et al. Guidelines for the welfare and use of animals in cancer research. *British journal of cancer* 102, 1555-1577, doi:10.1038/sj.bjc.6605642 (2010)). We observed that the mice appeared slightly ruffled during the last 2-3 days of treatment with the highest tested dose, in the absence of any other clinical signs, behavioral abnormalities or weight loss, and therefore we did not further increase the dose.

Hydrocotarnine (Indofine Chemical Company, NJ, USA) was dissolved in PBS to a concentration of 80 g/mL and mice received daily i.p. injections at a dose of 0.4 mg/kg bodyweight for 14 days post αCTLA4 treatment (Ito, K. et al. Effect of hydrocotarnine on cytochrome P450 and P-glycoprotein. *Drug metabolism and pharmacokinetics* 24, 108-113 (2009)).

Fasudil (Selleck Chemicals, Tx, USA) was dissolved to 2 mg/ml in distilled $H_2O$ and placed in drinking water of mouse cage from day of αCTLA4 treatment, for 14 days (Ying, H. et al. The Rho kinase inhibitor fasudil inhibits tumor progression in human and rat tumor models. *Molecular cancer therapeutics* 5, 2158-2164, doi:10.1158/1535-7163.MCT-05-0440 (2006)).

Galantamine (Abcam, Tx, USA) was dissolved to a concentration of 1 mg/mL in PBS. Mice received daily i.p. injections at a dose of 5 mg/kg bodyweight for 10 days post αCTLA4 treatment (Satapathy, S. K. et al. Galantamine alleviates inflammation and other obesity-associated complications in high-fat diet-fed mice. *Molecular medicine* 17, 599-606, doi:10.2119/molmed.2011.00083 (2011)).

Pyridoxine (Abcam, Tx, USA) was dissolved to a concentration of 20 mg/mL in PBS. Mice received daily i.p. injections at a dose of 100 mg/kg bodyweight for 7 days post αCTLA4 treatment (Franca, D. S. et al. B vitamins induce an antinociceptive effect in the acetic acid and formaldehyde models of nociception in mice. *European journal of pharmacology* 421, 157-164 (2001)).

PHA665752 (Selleck Chemicals, Tx, USA) was dissolved to a concentration of 10 mg/mL in DMSO. Mice received daily i.p. injections at a dose of 25 mg/kg bodyweight for 6 days post αCTLA4 treatment.

Adiphenine (Sigma, MO, USA) was dissolved in PBS to a concentrations of 1 mg/mL. Mice received daily i.p. injections of 100 µg/mouse for 10 days post αCTLA4 treatment.

Flavopiridol (Cayman Chemicals, Mic, USA) was dissolved in DMSO to a concentration of 3 mg/mL. Mice received daily i.p. injections at a dose of 7.5 mg/kg bodyweight for 10 days post αCTLA4 treatment.

Tomatidine (Sigma, MO, USA) was dissolved in PBS to a concentration of 5 mg/mL. Mice received daily dosing of 50 mg/kg bodyweight by oral gavage for 10 days post αCTLA4 treatment (Fujiwara, Y. et al. Triterpenoids isolated from *Zizyphus jujuba* inhibit foam cell formation in macrophages. *Journal of agricultural and food chemistry* 59, 4544-4552, doi:10.1021/jf200193r (2011)).

Protoporhyrin IX zinc(II) (Sigma, MO, USA) was dissolved in DMSO to a concentration of 20 mg/mL. Mice received daily i.p. injections at a dose of 50 mg/kg bodyweight for 7 days post αCTLA4 treatment.

JS-K (Sigma, MO, USA) was dissolved to 260 ug/mL in DMSO. Mice received daily i.p. injections for up to 10 days at 650 ug/kg after αCTLA4 treatment (day 10 post-incoulation). JS-K is a GST-activated nitric oxide generator (a prodrugs that release NO on metabolism by Glutathione S-Transferases), a drug that is in development for some forms of leukemia (Shami, P J et al. Leuk Res 2009; 33(11):1525-29)

During treatment mice weights were closely monitored and culled if significant weight loss (≥20% from starting weight) or other significant toxicity was observed.

Mice that were tumor-free for more than 3 months after treatment, were re-challenged with $5 \times 10^5$ AB1 mesothelioma cells that did not express the HA antigen. All animals rejected this second challenge, indicating that the anti-CTLA-4/drug-induced rejection of the AB1-HA tumor was not dominated by a T cell response towards the HA neo-antigen, which is in line with previously published findings (Marzo, A. L., Lake, R. A., Robinson, B. W. & Scott, B. T-cell receptor transgenic analysis of tumor-specific CD8 and CD4 responses in the eradication of solid tumors. *Cancer Res* 59, 1071-1079 (1999)).

Recombinant Cytokines for In Vivo Treatment

Recombinant murine IL-12 (Peprotech, NJ, USA), IL-18 (Novus Biologicals, CO, USA), IL-1β (Novus Biologicals, CO, USA) and IFNγ (Peprotech, NJ, USA) were diluted in PBS and injected i.p. in the following dosages/schedules: IL-12, 0.2 μg/g for 10 days post αCTLA4 treatment; IL-18 0.4 μg/g for 10 days post αCTLA4 treatment; IL-1β 0.5 μg/g for 10 days post αCTLA4 treatment and IFNγ 2 μg/g for 10 days post αCTLA4 treatment.

Statistical Analyses of Mouse Experiments

Data were analyzed using Prism 4.0 (GraphPad Software, Inc.). Tumor growth data were analyzed using the PASW statistics version 18 MIXED procedure (IBM SPSS, Chicago Ill.). Comparisons between treatment groups at each time point were adjusted for multiple comparisons by the Sidak method. Data for tumor survival were analyzed according to the Kaplan Meier method and survival proportions were compared between groups using a Log Rank Test.

The invention claimed is:

1. A therapeutic combination for use in the treatment of a malignant condition, the combination comprising one or more immune checkpoint modulating agents, and a therapeutic agent, wherein:
   (i) the one or more immune checkpoint modulating agents are selected from the group consisting of:
      (a) an inhibitor of CTLA-4;
      (b) an inhibitor of programmed cell death receptor (PD-1);
      (c) an inhibitor of PD Ligand 1; and
      (d) an activator of glucocorticoid-induced tumor necrosis factor receptor-related protein (GITR); and
   (ii) the therapeutic agent is selected from the group consisting of: a retinoid, retinoic acid receptor-γ agonist, pan-retinoic acid receptor agonist, retinoic acid receptor-α agonist, and a nitric oxide generator.

2. A therapeutic combination for use in the treatment of a malignant condition according to claim 1, wherein the condition is a cancer and/or tumor.

3. A therapeutic combination for use in the treatment of a malignant condition according to claim 2, wherein the condition is selected from: a melanoma, prostate cancer, lymphoma, mesothelioma, brain cancer, lung cancer and kidney cancer.

4. A therapeutic combination according to claim 1, wherein the combination consists essentially of one or more immune checkpoint modulating agents and the therapeutic agent.

5. A therapeutic combination for use according to claim 1, wherein the therapeutic agent is selected from the group consisting of: all-trans-retinoic acid, bexarotene, CD1530, Ro 41-5253, isosorbide dinitrate, isosorbide mononitrate, nitroglycerin, and JS-K.

6. A therapeutic combination for use according to claim 1, wherein the one or more immune checkpoint modulating agents comprises an inhibitor of CTLA-4.

7. A therapeutic combination for use according to claim 1, wherein the one or more immune checkpoint modulating agents comprises an inhibitor of PD-1.

8. A therapeutic combination for use according to claim 1, wherein the one or more immune checkpoint modulating agents comprises an inhibitor of PD Ligand 1.

9. A therapeutic combination for use according to claim 1, wherein the one or more immune checkpoint modulating agents comprises an activator of GITR.

10. A therapeutic combination for use according to claim 1, wherein the one or more immune checkpoint modulating agents is selected from the group consisting of: ipilimumab, tremelimumab, nivolumab, AMP-224, pidilizumab, pembrolizumab, MPDL-3280A, MSB0010718C, MEDI4736, TRX518 and MK4166.

11. A therapeutic combination according to claim 1, wherein the therapeutic combination is for use in the treatment of mesothelioma and the therapeutic agent is a nitric oxide generator or a retinoid.

12. A therapeutic combination according to claim 1, wherein the one or more immune checkpoint modulating agents comprises an inhibitor of CTLA-4 and the nitric oxide generator is selected from the group consisting of isosorbide dinitrate and JS-K.

13. A therapeutic combination according to claim 1, wherein the one or more immune checkpoint modulating agents comprises an inhibitor of CTLA-4 and the retinoid is all-trans retinoic acid.

14. A therapeutic combination according to claim 1, wherein the one or more immune checkpoint modulating agents comprises an activator of GITR and the therapeutic agent is selected from the group consisting of isosorbide dinitrate and all-trans retinoic acid.

15. A method of treating a malignant condition in a subject comprising the step of administering a therapeutically effective amount of a therapeutic combination according to claim 1 to a subject with a malignant condition.

16. The method of claim 15, wherein the malignant condition is selected from: a melanoma, prostate cancer, lymphoma, mesothelioma, brain cancer, lung cancer and kidney cancer.

17. The method of claim 15, wherein the combination consists essentially of the one or more immune checkpoint modulating agents and the therapeutic agent.

18. The method of claim 16, wherein the one or more immune checkpoint modulating agents comprises an inhibitor of CTLA-4 and the nitric oxide generator is selected from the group consisting of isosorbide dinitrate and JS-K.

19. The method of claim 16, wherein the one or more immune checkpoint modulating agents comprises an inhibitor of CTLA-4 and the retinoid is all-trans retinoic acid.

20. The method of claim 16, wherein the one or more immune checkpoint modulating agents comprises an activator of GITR and the therapeutic agent is selected from the group consisting of isosorbide dinitrate and all-trans retinoic acid.

21. A therapeutic combination according to claim 1, wherein the one or more immune checkpoint modulating agents comprises an inhibitor of PD-1 and the therapeutic agent is all-trans retinoic acid.

22. A therapeutic combination according to claim 1, wherein the one or more immune checkpoint modulating agents comprises an inhibitor of PD-L1 and the therapeutic agent is all-trans retinoic acid.

23. The method of claim 16, wherein the one or more immune checkpoint modulating agents comprises an inhibitor of PD-1 and the therapeutic agent is all-trans retinoic acid.

24. The method of claim 16, wherein the one or more immune checkpoint modulating agents comprises an inhibitor of PD-L1 and the therapeutic agent is all-trans retinoic acid.

* * * * *